(12) United States Patent
Zipse et al.

(10) Patent No.: US 7,994,169 B2
(45) Date of Patent: Aug. 9, 2011

(54) 3,4-DIAMINOPYRIDINE DERIVATIVES FOR USE AS CATALYSTS

(75) Inventors: Hendrik Zipse, Gauting (DE); Ingmar Held, Munich (DE)

(73) Assignee: Bayer MaterialScience AG, Leverkusen (DE)

(*) Notice: Subject to any disclaimer, the term of this patent is extended or adjusted under 35 U.S.C. 154(b) by 122 days.

(21) Appl. No.: 11/999,663

(22) Filed: Dec. 6, 2007

(65) Prior Publication Data
US 2008/0176747 A1 Jul. 24, 2008

(30) Foreign Application Priority Data

Dec. 6, 2006 (DE) ........................ 10 2006 057 580

(51) Int. Cl.
*A61K 31/50* (2006.01)
*A61K 31/495* (2006.01)
(52) U.S. Cl. ...................... 514/249; 544/353
(58) Field of Classification Search .................. 514/249; 544/353

See application file for complete search history.

(56) References Cited

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Couture, et al. Synthesis, 11, 1991, 982-984.*
Boutte, et al. Comptes Rendus des Seances de I'Academie des Sciences, Serie C: Sciences Chimiques, 273(22), 1971, 1529-1532.*
Armand, et al. Can. J. Chem. 66(5), 1988, 1500-1505.*
Hoefle et al., "4-Dialkylaminopyridine als hochwirksame Acylierungskatalysatoren", *Angew Chem.*, vol. 90, pp. 602-615 (1978).
Hoefle et al., "4-Dialkylaminopyridines as Highly Active Acylation Catalysts", *Angew. Chem., Int. Ed. Engl.*, vol. 17, pp. 569-583 (1978).
Ragnarsson et al., "Novel Amine Chemistry Based on DMAP-Catalyzed Acylation", *Acc. Chem. Res.*, vol. 31, pp. 494-501 (1998).
Spivey et al., "Asymmetric Catalysis of ACYL Transfer by Lewis Acids and Nucleophiles, A Review.", *Organic Preparations and Procedures Int.*, vol. 32 (4), pp. 331-365 (2000).
Berry et al., "Catalysis by 4-dialkylaminopyridines", *Reilly Industries Inc.*, pp. 201-226 (2001).
Spivey et al., "Nucleophile Katalyse durch 4-(Dialkylamino)pyridine neu aufgerolit: Optimierung von Reaktivitaet and Selektivitaet", *Angew. Chem.*, vol. 116, pp. 5552-5557 (2004).
Spivey et al., "Nucleophilic Catalysis by 4-(Dialkylamino)pyridines Revisited—The Search for Optimal Reactivity and Selectrivity", *Angew Chem, Int, Ed.*, vol. 43, pp. 5436-5441 (2004).
Vedejs et al., "Effizienz in der nichtenzymatischen kinetischen Racematspaltung", *Angew. Chem.*, vol. 117, pp. 4040-4069 (2005).
Vedejs et al., "Efficiency in Nonenzymatic Kinetic Resolution", *Angew. Chem. Ind. Ed.*, vol. 44, pp. 3974-4001 (2005).

Dalko et al., "Im Goldenen Zeitalter der Organokatalyse", *Angew. Chem.*, vol. 116, pp. 5248-5286 (2004).
Dalko et al., "In the Golden Age of Organocatalysis", *Angew. Chem. Int. Ed.*, vol. 43, pp. 5138-5175 (2004).
Fu, "Asymmetric Catalysis with "Planar-Chiral" Derivatives of 4-(Dimethylamino)pyridine", *Acc. Chem. Res.*, vol. 37, pp. 542-547 (2004).
France et al., "Nucleophilic Chiral Amines as Catalysts in Asymmetric Synthesis", *Chem. Rev.*, vol. 103, pp. 2985-3012 (2003).
Fu et al., "Enantioselective Nucleophilic Catalysis with "Planar-Chiral" Heterocycles", *Acc. Chem. Res.*, vol. 33, pp. 412-420 (2000).
Kawabata et al., "Remote Chirality Transfer in Nucleophilic Catalysis with N-(4-Pyridinyl)-L-Proline Derivatives", *Chirality*, vol. 15, pp. 71-76 (2003).
Kawabata et al., "Preparation and properties of chiral 4-pyrrolidinopyridine (PPY) analogues with dual functional side chains", *Tetrahedron Letters*, vol. 44, pp. 1545-1548 (2003).
Priem et al., "The Design of Novel N-4'-Pyridinyl-α-methyl Proline Derivatives as Potent Catalysists for the Kinetic Resolution of Alcohols", *J. Org. Chem.*, vol. 68, pp. 3844-3848 (2003).
Pelotier et al., "Convenient method for the kinetic resolution of β-aminoalcohols", *Tetrahedron Letters*, vol. 46, pp. 9005-9007 (2005).
Spivey et al., "Configurationally Stable Biaryl Analogues of 4-(Dimethylamino)pyridine: A Novel Class of Chiral Nucleophilic Catalysts", *J. Org. Chem.*, vol. 64, pp. 9430-9443 (1999).
Spivey et al., "Axially Chiral Analogues of 4-(Dimethylamino)pyridine: Novel Catalysts for nonenzymatic enantioselective Acylations", *J. Org. Chem.*, vol. 65, pp. 3154-3159 (2000).
Spivey, et al., "Synthesis of $C_2$-symmetric analogues of 4-(pyrolidino)pyridine: new chiral nucleophilic catalysts", *J. Chem. Soc., Perkin Trans.*, vol. 1, pp. 3460-3468 (2000).
Spivey et al., "Atropisomeric α-methyl substituted analogus of 4-(dimethylamino)pyridine: synthesis and evaluation as acyl transfer catalysts", *J. Chem. Soc., Perkin Trans.*, vol. 1, pp. 1785-1794 (2001).

(Continued)

*Primary Examiner* — James O. Wilson
*Assistant Examiner* — Douglas M Willis
(74) *Attorney, Agent, or Firm* — Connolly Bove Lodge & Hutz LLP (57) ABSTRACT

The present invention relates to 3,4-diaminopyridine derivatives of formula (I)

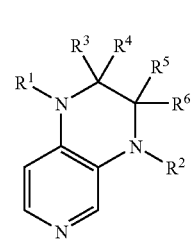

wherein
$R^1$ and $R^2$ are, independently of each other, electron donors, wherein R2 is optionally H; and
$R^3$, $R^4$, $R^5$, and $R^6$ are, independently of each other, H, optionally substituted straight-chain or branched alkyl, alkenyl, alkynyl, alkoxyl, or aryl, wherein $R^3$ and/or $R^4$ together with $R^5$ and/or $R^6$, optionally define a ring;
processes for their preparation, and their use as catalysts.

8 Claims, 2 Drawing Sheets

OTHER PUBLICATIONS

Malardier-Jugroot et al., Study of the influence of the non-pyridyl nitrogen hybridisation on the stability of axially chiral analgues of 4-(dimethylamino)pyridine (DMAP); *Journal of Molecular Structure (Theochem)*, vol. 623, pp. 263-276 (2003).

Spivey et al., "New atropisomeric biaryl derivatives of 4-aminopyridine-identification of an improved nucleophilic catalyst for asymmetric acylation of *sec*-alcohols", *Tetrahedron*, vol. 60, pp. 4513-4525 (2004).

Spivey et al., "Rapid, room-temperature acylative kinetic resoluton of sec-alcohols using atropisomeric 4-aminopyridine/triphenylphosphine catalysis", *Tetrahedron*, vol. 62, pp. 295-301 (2006).

Ó Daláigh et al., "Kinetic resolution of *sec*-alcohols using a new class of readily assembled (S)-proline-derived 4-(pyrrolidono)-pyridine analogues", *Org. Biomol. Chem.*, vol. 3, pp. 981-984 (2005).

Ó Daláigh et al., "Asymmetric acyl-transfer promoted by readily assembled chiral 4-*N*,*N*-dialkylaminopyridine derivatives", *Org. Biomol. Chem.*, vol. 4, pp. 2785-2793 (2006).

Shaw et al., "Development of Chiral Nucleophilic Pyridine Catalysts: Applications in Asymmetric Quaternary Carbon Synthesis", *J. Am. Chem. Soc.*, vol. 125, pp. 13368-13369 (2003).

Shaw et al., "Enantioselective TADMAP-Catalyzed Carboxyl Migration Reactions for the Synthesis of Sterogenic Quaternary Carbon", *J. Am Chem. Soc.*, vol. 128, pp. 925-934 (2006).

Yamada et al., "Kinetic resolution of sec-alcohols by a new class of pyridine catalysts having a conformation switch system", *Tetrahedron Letters*, vol. 46, pp. 2239-2242 (2005).

Miller, "In Search of Peptide-Based Catalysts for for Asymmetric Organic Synthesis", *Accounts of Chemical Research*, vol. 37, No. 8, pp. 601-610 (2004).

Fierman et al., "Structure-Selectivity Relationships and Structure for a Peptide-Based Enantioselective Acylation Catalyst", *J. Am. Chem. Soc.*, vol. 126, pp. 6967-6971 (2004).

Evans et al., "Catalytic Enantioselective Synthesis of Sulfinate Esters through the Dynamic Resolution of tert-Butanesulfinyl Chloride", *J. Am. Chem. Soc.*, vol. 126, pp. 8134-8135 (2004).

Sculimbrene et al., "Asymmetric Syntheses of Phosphatidylinositol-3-Phosphates with Saturated and Unsaturated Side Chains through Catalytic Asymmetric Phosphorylation", *J. Am. Chem. Soc.*, vol. 126, pp. 13182-13183 (2004).

Morgan et al., "Chemistry and Biology of Deoxy-*myo*-inositol Phosphates: Stereospecificity of Substrate Interactions within an Archaeal and a Bacterial IMPase", *J. Am. Chem. Soc.*, vol. 126, pp. 15370-15371 (2004).

Lewis et al., "Desymmetrization of Glycerol Derivatives with Peptide-Based Acylation Catalysts", *Organic Letters*, vol. 7, No. 14, pp. 3021-3023 (2005).

Xu et al., "Streamlined Synthesis of Phosphatidylinositol (PI), PI3P, PI3,5P$_2$, and Deoxygenated Analogues as Potential Biological Probes", *J. Org. Chem.*, vol. 71, pp. 4919-4928 (2006).

Heinrich et al., "Steigerung der katalytischen Aktivitaet von 4-(Dialkylamino)pyridinen durch konformative Fixierung", *Angew. Chem.*, vol. 115, pp. 4975-4977 (2003).

Henrich et al., "Enhancing the Catalytic Activity of 4-(Dialkylamino)pyridines by Conformational Fixation", *Angew. Chem. Int. Ed.*, vol. 42, pp. 4826-2828 (2003).

Held et al., "The Stability of Acylpyridinium Cations and Their Relation to the Catalytic Activity of Pyridine Bases", *Synthesis*, No. 9, pp. 1425-1430 (2005).

\* cited by examiner

3,4-DIAMINOPYRIDINE DERIVATIVES FOR USE AS CATALYSTS

RELATED APPLICATIONS

This application claims benefit to German Patent Application No. 10 2006 057 580.6, filed Dec. 6, 2006.

BACKGROUND OF THE INVENTION

The present invention relates to 3,4-diaminopyridine derivatives, a process for preparing them and the use of these 3,4-diaminopyridine derivatives as catalysts.

Donor-substituted pyridines play a prominent role as nucleophilic catalysts in many synthetically important transformations such as the acylation of alcohols, amines or enolates. See, for example, G. Höfle, W. Steglich, H. Vorbrüggen, *Angew. Chem.* 1978, 90, 602-615; *Angew. Chem. Int. Ed. Engl.* 1978, 17, 569-583; E. F. V. Scriven, *Chem. Soc. Rev.* 1983, 12, 129-161; A. Hassner, in *Encyclopedia of Reagents for Organic Synthesis*, Wiley, Chichester, 1995, 2022-2024; U. Ragnarsson, L. Grehn, *Acc. Chem. Res.* 1998, 31, 494-501; A. C. Spivey, A. Maddaford, A. Redgrave, *Org. Prep. Proced. Int.* 2000, 32, 331-365; D. J. Berry, C. V. Digiovanna, S. S. Metrick, R. Murugan, *Arkivoc* 2001, 201-226; and A. C. Spivey, S. Arseniyadis, *Angew. Chem.* 2004, 116, 5552-5557; *Angew. Chem. Int. Ed. Engl.* 2004, 43, 5436-5441. Also see E. Vedejs, M. Jure, *Angew. Chem.* 2005, 117, 4040-4069; *Angew. Chem. Int. Ed. Engl.* 2005, 44, 3971-4001; P. I. Dalko, L. Moisan, *Angew. Chem.* 2004, 116, 5248-5286; *Angew. Chem. Int. Ed. Engl.* 2004, 43, 5138-5178. (c) G. Fu, *Acc. Chem. Res.* 2004, 37, 542-547; S. France, D. J. Guerin, S. J. Miller, T. Lectka, *Chem. Rev.* 2003, 103, 2985-3012; and A. C. Spivey, A. Maddaford, A. Redgrave, *Org. Prep. Proced. Int.* 2000, 32, 331-365. (f) G. Fu, *Acc. Chem. Res.* 2000, 33, 412-420.

Great progress has been achieved recently in kinetic racemate resolution experiments using appropriately substituted derivatives of (4-dimethylamino)pyridine 1 (DMAP) or (4-pyrrolidino)pyridine 2 (PPY) (See Scheme 1). Reports of this progress appear in T. Kawabata, R. Stragies, T. Fukaya, K. Fuji, *Chirality* 2003, 15, 71; T. Kawabata, R. Stragies, T. Fukaya, Y. Nagaoka, H. Schedel, K. Fuji, *Tetrahedron Lett.* 2003, 44, 1545; G. Priem, B. Pelotier, S. J. F. Macdonald, M. S. Anson, I. B. Campbell, *J. Org. Chem.* 2003, 68, 3844; B. Pelotier, G. Priem, S. J. F. Macdonald, M. S. Anson, R. J. Upton, I. B. Campbell, *Tetrahedron Lett.* 2005, 46, 9005; A. C. Spivey, T. Fekner, S. E. Spey, H. Adams, *J. Org. Chem.* 1999, 64, 9430, and literature cited there; A. C. Spivey, T. Fekner, S. E. Spey, *J. Org. Chem.* 2000, 65, 3154; A. C. Spivey, A. Maddafort, T. Fekner, A. J. Redgrave, C. S. Frampton, *J. Chem. Soc. Perkin Trans.* 1. 2000, 3460; A. C. Spivey, A. Maddafort, T. Fekner, D. P. Leese, A. J. Redgrave, C. S. Frampton, *J. Chem. Soc. Perkin Trans.* 1, 2001, 1785; C. Malardier-Jugroot, A. C. Spivey, M. A. Whitehead, *J. Mol. Struct. (THEOCHEM)* 2003, 623, 263; A. C. Spivey, D. P. Leese, F. Zhu, S. G. Davey, R. L. Jarvest, *Tetrahedron* 2004, 60, 4513; A. C. Spivey, S. Arseniyadis, T. Fekner, A. Maddaford, D. P. Lees, *Tetrahedron* 2006, 62, 295; C. O. Dalaigh, S. J. Hynes, D. J. Maher, S. J. Connon, *Org. Biomol. Chem.* 2005, 3, 981; C. O. Dalaigh, S. J. Hynes, J. E. O'Brien, T. McCabe, D. J. Maher, G. W. Watson, S. J. Connon, *Org. Biomol. Chem.* 2006, 4, 2785; S. A. Shaw, P. Aleman, E. Vedejs, *J. Am. Chem. Soc.* 2003, 125, 13368-13369; S. A. Shaw, P. Aleman, J. Christy, J. W. Kampf, P. Va, E. Vedejs, *J. Am. Chem. Soc.* 2006, 128, 925-934; and S. Yamada, T. Misono, Y. Iwai, *Tet. Lett* 2005, 46, 2239.

Despite these developments, the field remains somewhat unbalanced, with a variety of solutions being available for particular synthetic problems such as kinetic racemate resolution of secondary alcohols but other apparently similar challenges such as kinetic racemate resolution of primary or tertiary alcohols appearing virtually insoluble.

Scheme 1: Structural formulae of (4-dimethylamino)pyridine 1 and (4-pyrrolidino)pyridine 2.

In this situation, a modular catalyst concept which allows a broad range of structural variations within a single synthesis strategy appears highly desirable. Concepts of this type have been researched recently by Miller et al. for catalysts which are based on peptidic structures and use imidazole as active center. See for, example, S. J. Miller, *Acc. Chem. Res.* 2004, 37, 601-610, and references therein; M. B. Fierman, D. J. O'Leary, W. E. Steinmetz, S. J. Miller, *J. Am. Chem. Soc.* 2004, 126, 6967-6971; J. W. Evans, M. B. Fierman, S. J. Miller, J. A. Ellman, *J. Am. Chem. Soc.* 2004, 126, 8134-8135; B. R. Sculimbrene, Y. Xu, S. J. Miller, J. Am. Chem. Soc. 2004, 126, 13182-13183; A. J. Morgan, Y. K. Wang, M. F. Roberts, S. J. Miller, *J. Am. Chem. Soc.* 2004, 126, 15370-15371; C. A. Lewis, B. R. Sculimbrene, Y. Xu, S. J. Miller, Org. Lett. 2005, 3021; Y. Xu, B. R. Sculimbrene, S. J. Miller, *J. Org. Chem.* 2006, 71, 4919-4928; and S. France, D. J. Guerin, S. J. Miller, T. Lectka, *Chem. Rev.* 2003, 103, 2985-3012.

Peptides are also the variable structural element in PPY derivatives developed by Kawabata et al. and by Campbell et al. See, e.g., T. Kawabata, R. Stragies, T. Fukaya, K. Fuji, *Chirality* 2003, 15, 71; T. Kawabata, R. Stragies, T. Fukaya, Y. Nagaoka, H. Schedel, K. Fuji, *Tetrahedron Lett.* 2003, 44, 1545; G. Priem, B. Pelotier, S. J. F. Macdonald, M. S. Anson, I. B. Campbell, *J. Org. Chem.* 2003, 68, 3844; B. Pelotier, G. Priem, S. J. F. Macdonald, M. S. Anson, R. J. Upton, I. B. Campbell, *Tetrahedron Lett.* 2005, 46, 9005. In all of these cases, the peptidic structures influence the course of the reaction by means of additional catalysts which are built up between substrates and the side chains in the rate-determining step of the catalysis cycle. However, the electronic character of the nucleophilic catalysis center is generally not altered by the variations of the peptide structures.

The modular construction of 3-substituted derivatives of 1 and 2, on the other hand, has the potential to modify both the nucleophilicity of the pyridine ring and also its side asymmetry. Experiments carried out to date have been restricted to examining stereodifferentiating processes.

Earlier studies on the catalytic potential of donor-substituted pyridines in acylation reactions have already indicated the relative stability of acylpyridinium cations 4Ac as qualitative criterion for the catalytic activity. See, for example, M. R. Heinrich, H. S. Klisa, H. Mayr, W. Steglich, H. Zipse, *Angew. Chem.* 2003, 115, 4975-4977; *Angew. Chem. Int. Ed.*

2003, 42, 4826-4828; and I. Held, A. Villinger, H. Zipse, *Synthesis* 2005, 1425-1426.

Scheme 2: Acyl transfer reaction (1) from a acylpyridinium cation to a substituted pyridine.

SUMMARY OF THE INVENTION

It is therefore an object of the present invention to provide compounds which allow a broad range of structural variations when used as catalyst within a single synthesis strategy. A further object of the present invention is to provide compounds which are simple to prepare in a broad range of structural variations. It is also an object of the present invention to provide compounds which can be used as catalysts for acylation reactions and for preparing urethanes and polyurethanes.

These objects are achieved by the invention described more fully below.

DETAILED DESCRIPTION OF THE INVENTION

The inventors of the present invention have surprisingly found that 3,4-diaminopyridine derivatives are easy to prepare and have advantageous properties when used as catalysts.

A first aspect of the present invention relates to a 3,4-diaminopyridine derivative of the formula I below where
$R^1$ and $R^2$ each represent, independently of one another, electron donors, with $R^2$ also being able to represent H; and
$R^3$, $R^4$, $R^5$ and $R^6$ are each selected independently from among H, substituted or unsubstituted, straight-chain or branched alkyl, alkenyl, alkynyl, alkoxy and substituted or unsubstituted aryl, with the radicals $R^3$ and/or $R^4$ together with the radicals $R^5$ and/or $R^6$ being able to form a ring.

In particular, the 3,4-diaminopyridine derivatives of the present invention are, due to the wide variability of the electronic properties of the pyridine ring, suitable as catalysts which can be used for a variety of purposes. The bridging ethylene unit between the two nitrogen atoms in the 3 and 4 positions of the pyridine ring can exert an advantageous electron-pushing effect on the pyridine ring. The ethylene bridge can bear one or more substituents. At least the nitrogen atom in the 4 position of the pyridine ring is fully substituted, i.e. it no longer bears a hydrogen atom.

A preferred embodiment of the present invention is a 3,4-diaminopyridine derivative of the formula I wherein the electron donors $R^1$ and $R^2$ are each selected independently from among substituted or unsubstituted, straight-chain or branched alkyl, alkenyl, alkynyl, acyl, alkoxy and substituted or unsubstituted aryl, more preferably substituted or unsubstituted phenyl and benzyl, with $R^2$ also representing H.

As used herein, an electron donor is a substituent which increases the electron density at the respective substitution sites. The radicals $R^1$ and $R^2$ increase the electron density on the nitrogen atoms in positions 3 and 4 of the pyridine ring.

In the context of the present invention, the above-mentioned alkyl, alkenyl, alkynyl, acyl and alkoxy substituents are in each case defined, independently of one another, as follows.

The term "alkyl" means a saturated hydrocarbon radical. The alkyl radical is preferably substituted or unsubstituted, straight-chain or branched $C_1$-$C_{20}$-alkyl, more preferably $C_1$-$C_{10}$-alkyl, even more preferably $C_1$-$C_8$-alkyl, even more preferably $C_2$-$C_6$-alkyl and most preferably $C_3$-$C_5$-alkyl. Examples of such alkyl substituents are methyl, ethyl, n-propyl, isopropyl, n-butyl, sec-butyl and t-butyl.

The term "alkenyl" means a singly or multiply unsaturated radical, i.e. an alkyl radical having one or more double bonds. The alkenyl radical is preferably a substituted or unsubstituted, straight-chain or branched $C_2$-$C_{20}$-alkenyl, more preferably $C_2$-$C_{10}$-alkenyl, even more preferably $C_2$-$C_8$-alkenyl, even more preferably $C_3$-$C_6$-alkenyl and most preferably $C_3$-$C_5$-alkenyl.

The term "alkynyl" as used herein means a radical which is singly or multiply unsaturated by triple bonds, i.e. an alkyl radical having one or more triple bonds. The radical can additionally have one or more double bonds. The alkynyl radical is preferably substituted or unsubstituted, straight-chain or branched $C_2$-$C_{20}$-alkynyl, more preferably $C_2$-$C_{10}$-alkynyl, even more preferably $C_2$-$C_8$-alkynyl, even more preferably $C_3$-$C_6$-alkynyl and most preferably $C_3$-$C_5$-alkynyl.

The term "acyl" as used herein refers to a —C(O)—R group, where R is an alkyl, alkenyl, alkynyl or aryl radical as described above. Acyl is preferably a substituted or unsubstituted straight-chain or branched $C_1$-$C_{20}$-acyl, more preferably $C_1$-$C_{10}$-acyl, even more preferably $C_1$-$C_8$-acyl, even more preferably $C_2$-$C_6$-acyl and most preferably $C_3$-$C_5$-acyl, or a benzoyl group. A particularly preferred acyl radical is the acetyl radical.

The term "alkoxy" as used herein refers to an alkyl radical which is bound via an oxygen atom. The alkoxy radical is preferably substituted or unsubstituted, straight-chain or branched $C_1$-$C_{20}$-alkoxy, more preferably $C_1$-$C_{10}$-alkoxy, even more preferably $C_1$-$C_8$-alkoxy, even more preferably $C_2$-$C_6$-alkoxy and most preferably $C_3$-$C_5$-alkoxy. Examples of such alkyl substituents are methoxy, ethoxy, n-propoxy, iso-propoxy, n-butoxy, sec-butoxy and t-butoxy groups.

In a further embodiment of the present invention, at least one of the radicals $R^3$, $R^4$, $R^5$ and $R^6$ is not H. Here, preference is given to at least one of the radicals $R^3$, $R^4$, $R^5$ and $R^6$ being phenyl. Greater preference is given to the two radicals $R^3$ and $R^6$ each being H and the two radicals $R^4$ and $R^5$ together being 1,4-butanediyl so as to form a 6-membered ring as is shown by way of example in the compound 11 described below. However, it is also possible for this 6-membered ring to be an unsaturated or substituted ring.

Another preferred embodiment of the present invention is a 3,4-diaminopyridine derivative of the formula I in which the two radicals $R^4$ and $R^5$ are located in a cis position relative to one another so as to give a 3,4-diaminopyridine derivative of the formula Ia:

in which $R^1$ and $R^2$ are each, independently of one another, electron donors, with $R^2$ also being able to be H;

$R^3$ and $R^6$ are each selected independently from among H, substituted or unsubstituted, straight-chain or branched alkyl, alkenyl, alkynyl, alkoxy and substituted or unsubstituted aryl groups;

$R^4$ and $R^5$ are each selected independently from among substituted or unsubstituted, straight-chain or branched alkyl, alkenyl, alkynyl, alkoxy and substituted or unsubstituted aryl groups; and the radicals $R^3$ and/or $R^4$ together with the radicals $R^5$ and/or $R^6$ can form a ring.

In this embodiment, the two radicals $R^4$ and $R^5$ are located in a cis position relative to a plane formed by the atoms of the pyridine ring, the two nitrogen atoms in the positions 3 and 4 of the pyridine ring and the carbon atoms 8 and 9 of the bridging ethylene unit. If a plurality of substituents are present in the carbon atoms 8 and 9, i.e. at least two of the radicals $R^3$ and $R^4$ or $R^5$ and $R^6$ are not H, it is particularly preferred that, if the radicals $R^4$ and $R^5$ form a ring, this ring is present in a cis position. If there is no ring formation, preference is given to the two bulkier substituents among the radicals $R^3$, $R^4$, $R^5$ and $R^6$ to be present in a cis position on the carbon atoms 8 and 9.

In a particularly preferred 3,4-diaminopyridine derivative, $R^1$ and $R^2$ are each ethyl, $R^3$ and $R^5$ are each H and $R^4$ and $R^6$ together are 1,4-butanediyl so as to form a 6-membered ring. This compound is designated as 11 herein.

In another preferred embodiment of the present invention, $R^1$ and $R^2$ are each, independently of one another, a substituted or unsubstituted, straight-chain or branched $C_1$-$C_{10}$-alkyl, preferably a substituted or unsubstituted, straight-chain or branched $C_2$-$C_8$-alkyl and most preferably a substituted or unsubstituted, straight-chain or branched $C_3$-$C_6$-alkyl group.

A second aspect of the present invention relates to a process for preparing a 3,4-diaminopyridine derivative of the formula I in which (a) 3,4-diaminopyridine is reacted with a 1,2-dicarbonyl compound; (b) the resulting diimine is reduced to the corresponding diamine; and (c) at least the hydrogen atom on the nitrogen is replaced in the 4 position of the pyridine ring.

The 1,2-dicarbonyl compound is preferably a compound of the formula II shown below In a preferred embodiment of the second aspect, both the nitrogen atoms in positions 3 and 4 of the pyridine ring are substituted.

Preference is given to alkyl substitution on the nitrogen atoms of positions 3 and/or 4 of the pyridine ring being effected by means of a two-stage synthesis comprising acylation of the nitrogen atom and subsequent reduction of the resulting amide to an amine. If further substituents $R^3$ and $R^6$ are to be introduced, this is preferably effected during the reduction of the diimine by means of anionic alkyl groups.

A third aspect of the present invention relates to the use of a 3,4-diaminopyridine of the formula I above as catalyst in a chemical reaction. This chemical reaction is preferably an acylation reaction, in particular an acylation reaction of an alcohol or an amine, or a urethane and/or polyurethane synthesis. The 3,4-diaminopyridines of the present invention can advantageously catalyze the reaction of an isocyanate with an alcohol. The 3,4-diaminopyridines of the present invention are therefore useful in the synthesis of urethanes and/or polyurethanes.

In the customary use of a catalyst, the 3,4-diaminopyridines of the present invention are added to the reagents and solvent(s) necessary for the reaction to be catalyzed. These can be the reagents necessary for an acylation reaction or a urethane and/or polyurethane preparation.

The compounds of the present invention can also be used advantageously for preparing a pharmaceutical agent or a herbicide.

The present invention will now be more particularly described with the aid of examples and reference to the accompanying figures.

The development of catalysts based on the 3,4-diaminopyridine moiety has been aided by a theoretical estimate of the stability of the corresponding acyl intermediates, which can be expressed quantitatively by the enthalpy of reaction for the homodesmic acyl transfer reaction (1) (see Scheme 2).

The enthalpies of reaction for a number of 3,4-diaminopyridines are shown in Table 1 together with the values for other pyridine derivatives whose catalytic potential is already known from earlier studies. These include pyridine (4), DMAP (1), PPY (2) and tricyclic DMAP derivative 5, which are all outside the scope of the present invention. The results shown in Table 1 are depicted in graph form in FIG. 1.

TABLE 1

| System | $\Delta H_{rxn}(298)$ [kJ mol$^{-1}$] | Charge q(Ac)[a,b] | Distance r(C—N)[b] [pm] |
|---|---|---|---|
| 4 | 0.0 | +0.366 | 153.38 |
| 18 | −39.0 | +0.318 | 149.70 |
| 14 | −46.2 | +0.321 | 149.96 |
| 8 | −48.7 | +0.324 | 150.09 |
| 17 | −57.3 | +0.294 | 148.71 |
| 7 | −67.1 | +0.310 | 149.26 |
| 13 | −73.1 | +0.305 | 148.99 |
| 16 | −82.0 | +0.299 | 148.71 |
| 1 | −82.1 | +0.298 | 148.16 |

TABLE 1-continued

| System | $\Delta H_{rxn}(298)$ [kJ mol$^{-1}$] | Charge q(Ac)$^{a,b}$ | Distance r(C—N)$^b$ [pm] |
|---|---|---|---|
| 21 | −85.5 | +0.301 | 148.60 |
| 2 | −93.1 | +0.291 | 147.86 |
| 12 | −103.2 | +0.291 | 148.18 |
| 6 | −105.0 | +0.284 | 147.66 |
| 5 | −108.9 | +0.279 | 147.07 |
| 20 | −115.5 | +0.278 | 147.31 |
| 19 | −116.5 | +0.274 | 147.16 |
| 10 | −117.9 | +0.277 | 147.46 |
| 9 | −119.2 | +0.277 | 147.29 |
| 15 | −122.2 | +0.274 | 147.12 |
| 11 | −127.1 | +0.272 | 147.06 |

Table 1. Enthalpies of reaction $\Delta H_{rxn}(298)$ at 298.15 K for the acetyl transfer reaction according to equation (1) of Scheme 1, which were calculated on the B3LYP/6-311 + G(d,p)// B3LYP/6-31G(d) level (in kJ mol$^{-1}$).
$^a$in units of the charge on the element e;
$^b$charge and distance parameters are always based on the most favorable conformer.

The structurally simplest 3,4-diaminopyridine considered here is 6, which is based on the tetrahydropyrido[3,4-b]pyrazine skeleton. The stability of the corresponding acetyl intermediate 6Ac is close to that of the more highly catalytically active 5. Replacement of the two methyl groups in 6 by one (in 7 and 21) or two (as in 8) acetyl group(s) reduces the electron density in the pyridine ring and thus also the stability of the corresponding cations 7Ac and 8Ac quite significantly. The stability difference between 6Ac and 21Ac (19.5 kJ mol$^{-1}$) and between 6Ac and 7Ac (37.9 kJ mol$^{-1}$) shows that the nitrogen in the 4 position is significantly more sensitive to changes in the substitution pattern than the nitrogen in the 3 position. The combined effect of the two substituents in 8 (56.3 kJ mol$^{-1}$ relative to 6) is virtually identical to the sum of the two individual substituents (57.4 kJ mol$^{-1}$). Replacement of the two methyl groups in 6 by ethyl groups increases the stability of the acetyl intermediate by 10 kJ mol$^{-1}$. Fusion of a saturated alkyl ring onto the system 6 in either the cis orientation (as in 9) or the trans orientation (as in 10) likewise increases the stability of the acetyl intermediate by about 15 kJ mol$^{-1}$. The stability of the acetylpridinium cations derived from the tricyclic systems 9 and 10 depends on the N substituents in a way similar to that described for the bicyclic system 6. Introduction of two ethyl groups thus leads to the most stable acetyl intermediates 11Ac and 15Ac. Finally, introduction of aryl substituents into the ethylene bridge of 6 (for instance as in 19) also increases the stability of the corresponding cationic intermediate, which is probably due to inductive electron transfer to the 3,4-diamino nitrogen atoms. The stability values for the acetyl intermediates of the compounds in FIG. 1 cover a range of virtually 90 kJ mol$^{-1}$. In the case of the compounds 1, 2 and 5, it has been found that their stability values are related to the catalytic activity. Without wishing to be tied to a theory, it would be expected that the stability values of the 3,4-diaminopyridines 18 and 11 (which mark the two ends of the scale) would differ in terms of their catalytic activity by a factor of 30. Furthermore, a glance at the charge and distance data in Table 1 shows that greater thermodynamic stability corresponds with shorter C—N bond lengths and smaller acetyl group charges.

Figure 1:
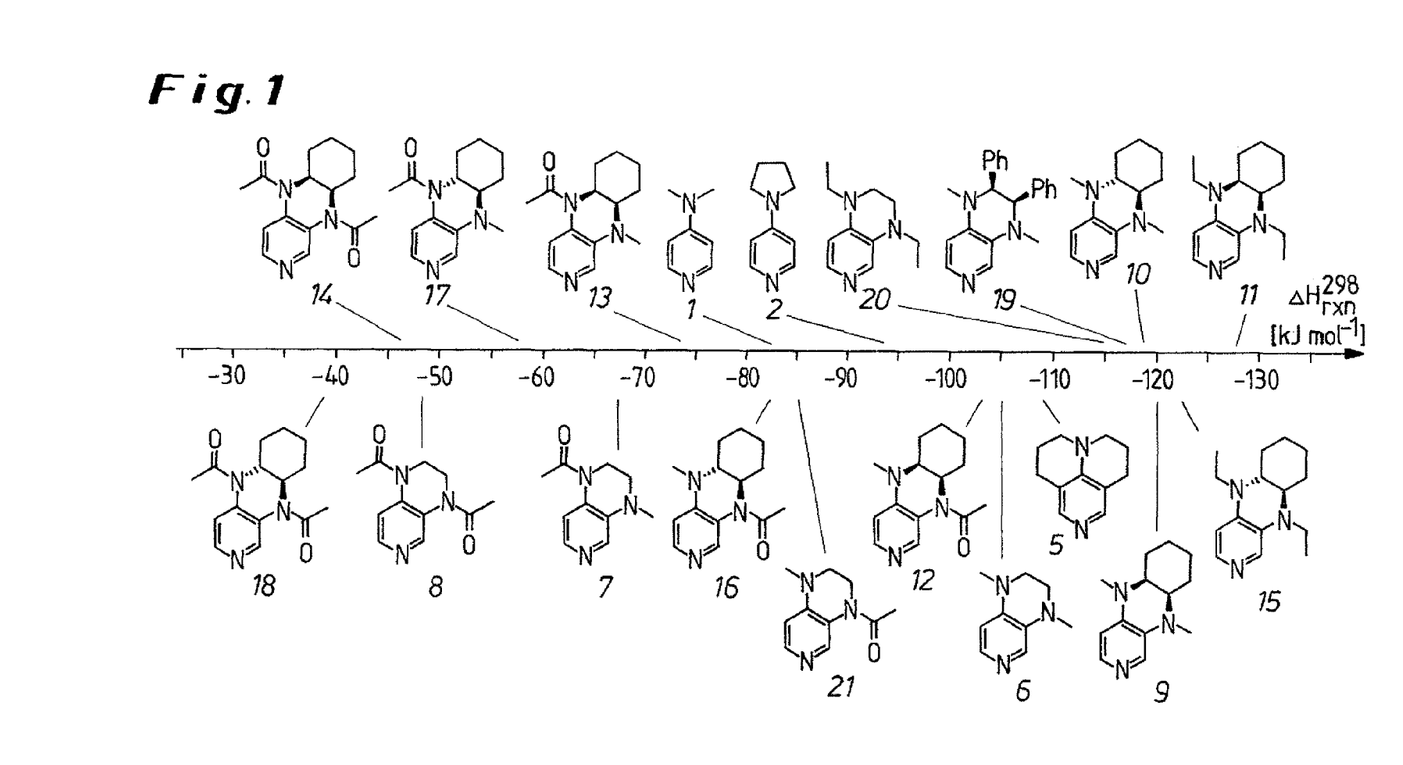
FIG. 1 shows the enthalpies of reaction for 3,4-diaminopyridines 6-21 in comparison with the pyridines 1, 2 and 5 according to equation (1) of Scheme 1.

Some of the compounds shown in FIG. 1 can be prepared efficiently from 3,4-diaminopyridine 22 in a 3- to 5-stage sequence. (See Scheme 3.) Condensation of 22 with glyoxal, 1,2-cyclohexadione or benzil lead to good yields of the diimines 23-25. (See, e.g., W. W. K. R. Mederski, D. Kux, M. Knoth, M. J. Schwarzkopf-Hofmann, *Heterocycles*, 2003, 4, 925-931.) Pyridopyrazine 23 (R=H) could subsequently be reduced to the tetrahydro derivative 26 (See, e.g., J. Armand, L. Boulares, C. Bellec, J. Pinson, *Can J. Chem.* 1988, 66, 1500-1505.) and alkylated under Eschweiler-Clark conditions to form the compound 6. (See, e.g., 14, M. L. Moore, *Org. React.* 1949, 5, 301-330.) The introduction of longer alkyl chains is effected more efficiently by means of a two-stage sequence comprising an introductory bis-acylation and subsequent reduction to the corresponding diamine. (See, e.g., C. Sotirou-Leventis, Z. Mao, A.-M. M. Rawashdeh, *J. Org. Chem.* 2000, 65, 6017-6023.) Starting from 26, the diethylated compound 20 could be prepared in a yield of 48% in this way. A similar procedure allows the synthesis of the cyclohexyl-fused system 11 which is obtained from the diamine 27 in two steps in a yield of 37%. The cis-fused diamine 27 can also be obtained from 24 in a yield of 74% by selective reduction using NaBH$_4$/BH$_3$/H$_2$NCH$_2$CH$_2$OH. (See C. Kison, N. Meyer, T. Opatz, *Angew. Chem. Int. Ed.* 2005, 44, 5662-5664.) or in a yield of 90% by reduction using LiAlH$_3$ at −40° C. Use of the simpler reduction method used for the compound 26 leads in this case to a cis/trans mixture of 27.

Scheme 3. Synthesis of catalysts based on the 3,4-diaminopyridine moiety.

a) glyoxal, 1,2-cyclohexadienone or benzil, EtOH, 70° C., 5 h, 95-98%.
b) powdered NaBH$_4$, EtOH, 40° C., 24 h, 50%.
c) 200 eq. CH$_2$O (37% in water), 100 eq. HCO$_2$H, 110° C., 48 h, 57%.
d) (CH$_3$CO)$_2$O, pyridine, 100° C., 24 h, 80%.
e) 4.2 eq. LiAlH$_4$, 2.6 eq. AlCl$_3$, MTBE, 0° C., 1 h, then reflux, 8 h, 60%.
f) LiAlH$_4$, THF, -40 to RT, 32 h, 90%.
g) (CH$_3$CO)$_2$O, 25 mol% PPY, pyridine, 100° C., 48 h, 68%.
h) 4.2 eq. LiAlH$_4$, 2.6 eq. AlCl$_3$, MTBE, 0° C., 1 h, then reflux, 8 h, 55%.
i) 1.1 eq. (CH$_3$CO)$_2$O, 0.2 eq. 2, NEt$_3$, DCM, RT, 3 h, 82%.
j) 2.2 eq. LiAlH$_4$, 1.3 eq. AlCl$_3$, MTBE, 0° C., 1 h, then reflux, 8 h, 65%.
k) 1) 1 eq. n-BuLi, THF, -78° C., 1 h, then ° C., 1 h; 2) 1.1 eq. CH$_3$COCl, THF, -78° C., to RT, 1 h, 16%.
l) powdered NaBH$_4$, EtOH, 40° C., 48 h, 74%.
m) 88 eq. CH$_2$O (37% in water), 200 eq. HCO$_2$H, 110° C., 48 h, 90%.
n) 1) 1 eq. n-BuLi, MTBE, -78° C., 1 h, then 0° C., 1 h; 2) 1.1 eq. CH$_3$COCl, MTBE, -78 to 0° C., 1 h, 36%.
o) 2.2 eq. LiAlH$_4$, 1.3 eq. AlCl$_3$, THF, 0° C., 1 h, then reflux, 18 h, 53%.

Use of a milder acylation method for the reaction of 27 indicates a significantly higher reactivity of the C4 amino group, which explains the preferential formation of the amide 28 as only reaction product. Reduction of this amide as before to form the corresponding amine and acylation of the remaining amino function on C3 thus makes it possible to produce catalysts which contain two donor substituents of differing strengths. The influence of aryl substituents on the bridge connecting the two amino nitrogen atoms on C3 and C4 was examined by synthesis of the compound 34. While the reduction of the corresponding pyridopyrazine 25 can be carried out readily under the conditions used for 26, the subsequent Eschweiler-Clark alkylation stops at the monoalkylation stage to give the compound 32. The acetylation of 32 proved to be surprisingly difficult under all conditions previously used, but could finally be brought about by introductory deprotonation using n-BuLi, reaction of the amide anion with AcCl and subsequent reduction to form 34.

The composition of all compounds shown in Scheme 3 is demonstrated by high-resolution mass spectrometry. The structure of the pyridine ring can be derived for all compounds directly from the presence of three signals (one singlet, two doublets) in the appropriate region of the $^1$H-NMR spectrum (6.5-8 ppm). This leaves the problem of the stereochemical assignment of the cyclohexane fusion in the compounds 11, 14 and 27-30, and the regiochemical control of the N-alkylation and N-acylation reactions. The $^1$H-NMR signals for the adjacent protons H$_a$ and H$_e$ in structure 11 (See Scheme 4.) have a coupling constant of $^3J_{HH}$=2.8 Hz and display a positive NOE signal which can be reconciled with either an axial-equitorial arrangement or an equatorial-equatorial arrangement. (See Timothy D. W. Claridge, High-Resolution NMR Techniques in Organic Chemistry, *Tetrahedron Organic Chemistry Series,* 1999, 19, 298-299.) However, an equatorial-equatorial orientation of the two protons can be ruled out since the 3,4-diaminopyridine unit can hardly be bound to the cyclohexane ring by diaxial fusion.

Scheme 4. Arrows indicate observed NOE reinforcements.

Figure 2:
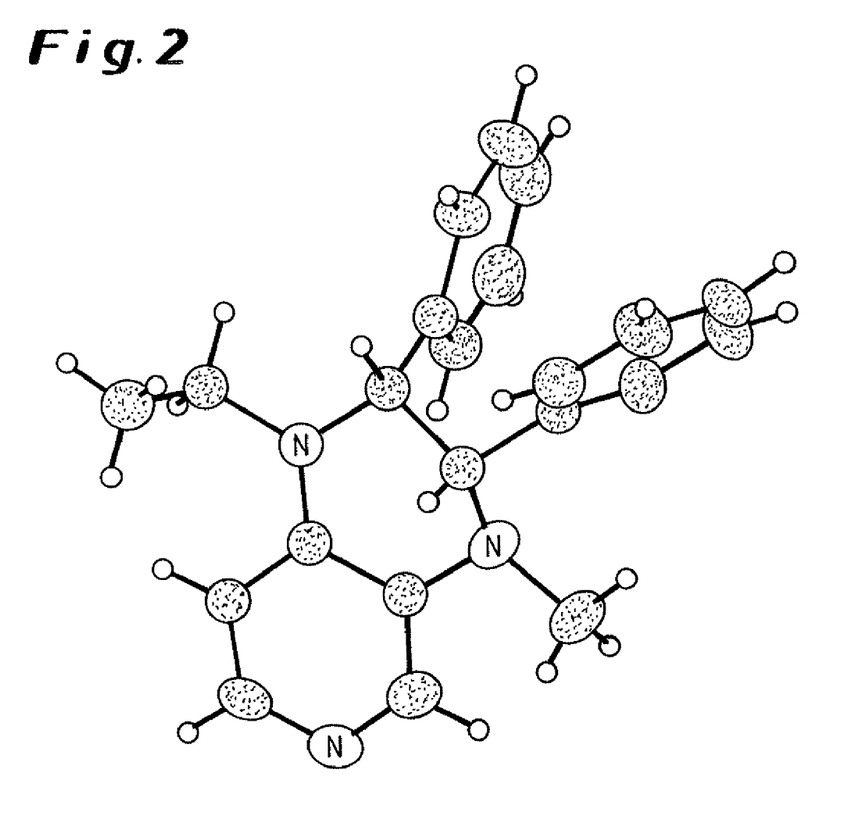
FIG. 2 shows the single-crystal X-ray structure of the compound 34.

The regioselectivity of the acetylation of 27 to form 28 could not be confirmed directly since the spectroscopic data of 28 were not informative in this respect. However, after reduction of 28 to 29, positive NOE signals between the ethyl group and the proton in the C5 position of the pyridine ring can be observed. This supports the structure shown in Scheme 3. The regiochemistry of the N-methylation of 31 to form 32 could likewise be established by observation of NOE reinforcements between the signals for the methyl group (2.85 ppm) and those for the proton at C1 of the pyridine ring (7.82 ppm) and one of the benzylic protons (4.44 ppm). Retention of this regiochemistry in the doubly alkylated product 34 could be confirmed without doubt by single-crystal X-ray structure analysis of this compound (See FIG. 2 crystallized from isohexane/dichloromethane).

Catalytic Properties

The catalytic properties of the pyridines 1, 2, 5, 6, 8, 11, 20 and 34 were examined in two acylation reactions A and B shown in Scheme 5.

Scheme 5: Acylation reactions A and B.

The tertiary alcohol 35 was used as model substrate in earlier studies because of its low reactivity. Acetylation of 35 by means of acetic anhydride (36) in the presence of triethylamine as auxiliary base (reaction A) proceeds quantitatively as long as a catalyst which has at least the reactivity of DMAP (1) is used in a concentration of 10% (relative to 35). The half life $\tau_{1/2}$ of the reaction can be determined by integration of the signals of the starting materials and products in the $^1$H-NMR spectrum and is used here as a measure of the catalytic activity. In reaction B, the same alcohol is reacted as before with isobutyric anhydride (38) as acylation reagent. Since this reaction proceeds significantly more slowly than that of 36, a higher reaction temperature (40° C.) was selected for the reaction. This choice leads to approximately similar half lives for the two reactions.

Based on recent studies on DMAP-catalyzed acylation reactions (See, S. Xu, I. Held, B. Kempf, H. Mayr, W. Steglich, H. Zipse, Chem. Eur. J. 2005, 11, 4751-4757; and C. B. Fischer, S. Xu, H. Zipse, Chem. Eur. J. 2006, 12, 5779-5784.), the mechanism shown in Scheme 6 can be assumed for both reactions in nonpolar solvents. Accordingly, anhydride and catalyst react in a first (usually rapid) initial step to form a complex of acylpyridinium cation and carboxylate anion. This complex can generally not be detected in the $^1$H-NMR spectrum under the conditions used here. It can therefore be asssumed that the corresponding equilibrium constant K is very small for both reactions A and B.

Scheme 6: Acylation mechansism according to reactions A and B.

In the rate-determining step, the acylpyridinium cation reacts with the alcohol 35 to form the ester product and the deactivated catalyst. This can be regenerated again by action of the auxiliary base NEt$_3$. The half lives $\tau_{1/2}$ measured here (Table 2) reflect the influence of the catalyst on both of the steps. A clear correlation of $\tau_{1/2}$ with the calculated stability values (Table 1) for the acetylpyridinium cations can therefore be expected only when the substituent effects on K are greater than those on k$_{cat}$.

TABLE 2

| Catalyst | A<br>$\tau_{1/2}$ (min) | B<br>$\tau_{1/2}$ (min) |
|---|---|---|
| 1 (DMAP) | 166 | 304 |
| 2 (PPY) | 75 | 171 |
| 5 | 21 (29) | 67 (86) |
| 6 | 56 | 129 |
| 8 | >38000[a] | >100000[a] |
| 11 | 24 (37) | 63 (81) |
| 20 | 53 | 91 |
| 30 | 138[b] | 112 |
| 34 | 144 | 269 |

Table 2. Reaction half lives $\tau_{1/2}$ (in min) for the model reactions A and B. The results in parentheses were obtained using Hünig base (EtN(i–Pr)$_2$) as auxiliary base.
[a]The reaction rate in this case bearly differs from that of the background reaction. This makes precise determination of the half lives by the methods used here exceptionally difficult. The data shown in Table 2 are obtained from conversion measurements for reaction A over 25 days, 17 hours and 30 minutes and for reaction B over 31 days, 17 hours and 15 minutes. In both cases, a conversion of 50% is not achieved within these times.
[b]The conversion in this reaction stops at 59%. ESI–MS studies on the reaction mixture indicate that the catalyst is no longer intact at this time.

The reactivity data for the compounds 1, 2 and 5 in Table 2 deviates somewhat from those for the same reaction under identical conditions in an earlier publication. This is partly due to small differences in the NMR measurements for following the reaction (See Examples). Furthermore, the results for relatively active catalysts such as 5 can only be reproduced when using extraordinarily pure samples. On the other hand, carrying out the reaction under strictly anaerobic conditions is not necessary. The results in Table 2 for the catalysts 6, 11 and 20 show that diaminopyridines are significantly more reactive than monosubstituted pyridines such as DMAP or PPY. The best results were obtained for compound 11 which has a similar activity to the above-mentioned carbocyclic compound 5. Comparison of the results for 20 and 11 shows a strong influence of the donor properties of the bridging moiety, while the difference between N-methyl or N-ethyl substitution (20 vs. 6) tends to have a small effect. While these results are completely in agreement with the stability values in Table 1 and FIG. 1, the catalytic activity of 34, measured by the stability value of the related compound 19, is surprisingly low. The catalytic activity is significantly reduced by the introduction of acceptor substituents, which is illustrated by the low activity of 30 (compared to 11) and also by the extremely slow reaction when using the N-acylated compound 8. While this was to be expected in view of the low stability value of the corresponding acetyl intermediate, the stability scale in FIG. 1 is not in agreement with the experimentally determined reactivity data in Table 2 in all cases. The dependence of the reactivity data on the choice of the substrates is made clear by comparison of the results for the reactions A and B. The reactivity ratio for the most active compound 11 and DMAP is 7.0 for reaction A and 4.8 for reaction B. A similar result is obtained for the pyridine derivative 5, which displays rectivity ratios of 7.9 and 4.5. The choice of the auxiliary base represents a further experimental variable which was examined for catalysts 5 and 11. It is surprisingly found that the catalytic efficiency for both catalysts decreases in a comparable fashion when using the stronger auxiliary base EtN(iPr)$_2$ (Hünig base) compared to NEt$_3$.

Alkyl-substituted 3,4-diaminopyridines represent a new class of catalysts for the acylation of alcohols. The catalytic efficiency of these compounds can be altered over a wide range within a single synthetic strategy by variation of the nitrogen substituents. The catalytic activity of the best of these catalysts is comparable with the best carbocyclic derivatives of DMAP known to date. In contrast to the latter compounds, the most active 3,4-diaminopyridine catalysts can be obtained in a simple fashion by means of a flexible 3- or 4-stage synthesis which can easily be modified for further structural variations.

EXAMPLES

Optimizations of the geometry were carried out using the Becke3LYP hybrid functional in combination with the split valence basis set 6-31G(d). Thermochemical enthalpy correction at a temperature of 298.15 K was carried out by means of a frequency calculation on the same level. Single-point calculations were carried out on the Becke3LYP/6-311+G(d, p) level. Combination of the energy obtained with the thermochemical correction on the Becke3LYP/6-31G(d) level gave the H$_{298}$ values described herein. All calculations were carried out using the Gaussian 03. See Gaussian 03, Revision B.03, M. J. Frisch, et al, Gaussian, Inc., Wallingford Conn., 2004.

All reactions which were carried out with exclusion of moisture were carried out under a nitrogen atmosphere in dry solvents and reaction apparatuses which had been dried by means of a drying oven and hair dryer. THF was distilled from sodium hydride under a nitrogen atmosphere. Methyl tert-butyl ether (MTBE), pyridine, triethylamine and deuterochloroform were distilled from calcium hydride under a nitrogen atmosphere. Acetic anhydride and isobutyric anhydride were distilled under reduced pressure from $P_4O_{10}$ onto dry $K_2CO_3$, filtered and fractionated under reduced pressure. Both anhydrides were stored over 4 Å molecular sieves under a nitrogen atmosphere. Ethanol, dichloromethane, ethyl acetate and methanol were distilled on a rotary evaporator. n-BuLi was titrated with diphenylacetic acid and the molarity was determined. All other reagents were, unless indicated otherwise, used in the highest possible quality without further purification. Thin layer chromatography was carried out on TLC plates marked with fluorescent dye from Merck KGaA (silica gel 60 $F_{254}$, layer thickness: 0.2 mm) and on Fluka plates (basic aluminum oxide $F_{254}$, Brockman activity: 1, pH: 9.5, layer thickness: 0.2 mm). Flash chromatography was carried out using Merck KGaA silica gel 60 (particle size: 0.040-0.063 mm) and Fluka basic aluminum oxide (basic aluminum oxide $F_{254}$, Brockman activity: 1, pH: 9.5, particle size: 0.05-0.15 mm) at a pressure of 1.5 bar for silica gel and 0.5 bar for basic aluminium oxide. $^1$H- and $^{13}$C-NMR spectra were recorded on Varian Mercury 200, Varian 300, Varian INOVA 400 and Varian 600 instruments. NOE spectra were recorded in $CDCl_3$ at 27° C. Chemical shifts were reported in ppm relative to the solvent peak. (See H. E. Gottlieb, V. Kotyar, A. Nudelman, *J. Org. Chem.* 1997, 21 7512-7515.)

The following abbreviations were used to characterize the multiplicities of the signal in the $^1$H-NMR spectrum: s=singlet, d=doublet, t=triplet, q=quartet, quin=quintet, sex=sextet, sep=septet, m=multiplet, b=broad and combinations of the abbreviations used. All $^1$H and $^{13}$C signals were assigned by means of COSY, NOESY, HSQC, HMBC and DEPT experiments. $^1$H-NMR spectra for the kinetic measurements were evaluated using the program VNMR 4.3 Rev. G0194. Integrals of the relevant peaks were evaluated. The subroutine was described using MAGICAL™ II programming. IR spectra were recorded on KBr pellets as sample medium using a Perkin-Elmer 1420 infrared spectrometer and a Perkin-Elmer FT-IR spectrum BX spectrometer using the ATR technique. All signals were reported as vs=very strong, s=strong, m=medium and w=weak. Mass spectra were recorded on a Finnigan MAT 95 using electron impact ionization (EI, 70 eV) or chemical ionization (CI, isobutane) as ion source. ESI-MS spectra were recorded using a Thermo Finnigan LTQ FT instrument. Gas chromatograms were recorded on a Varian 3400 GC with a 25 m CS-Supreme-5 capillary column and a Finnigan MAT 95 mass spectrometer as detector. In the case of the electron-rich pyridines 11, 5, 6, 20 and 32, the solvent was distilled off after flash chromatograhy by passing a stream of nitrogen into the rotary evaporator.

General Procedure for the Reactivity Experiments A and B.

Deuterochloroform, triethylamine and Hünig base were freshly distilled from calcium hydride under a nitrogen atmosphere before use. All kinetic measurements were recorded on a Varian Mercury 200 spectrometer at a constant temperature of 23° C. for reaction A and 40° C. for reaction B. The following standard solutions in deuterated chloroform were made up in three dry 5 ml volumetric flasks.

A: 1.2 M acetic anhydride solution.
B: 0.6 M ethynylcyclohexanol solution and 1.8 M triethylamine or Hünig base solution.
C: 0.06 M catalyst solution.

Sample preparation and kinetic measurement for reaction A. 200 μl of the above-mentioned standard solutions were in each case pipetted into an NMR tube by means of an Eppendorf pipette. The reaction mixture was mixed and immediately placed in the NMR spectrometer. The reaction was monitored by recording NMR spectra at defined time intervals to 100% conversion.

Sample preparation and kinetic measurement for reaction B. Procedure as described under reaction A except that the NMR tubes were flame sealed by means of a burner in order to prevent evaporation of the solvent.

Determination of the half life for reaction A. All signals which could be assigned to the protons of an acetyl group were integrated automatically after recording of the spectra. Acetic anhydride, ester and triethylammonium acetate were integrated within the following integral limits: ±8, ±2 and ±6 Hz. The conversion was calculated according to equation 2. The conversion was fitted as a function of time by means of equation 4 to self consistency. The half life was calculated at 50% conversion using function 4.

Determination of the half life for reaction B. The doublet of the isobutyric acid group and the signal of dioxane were integrated automatically after recording of the NMR spectra. Dioxane and isobutyric anhydride were integrated within the same integral limit of ±2 Hz. The conversion was calculated according to equation 3. The conversion was fitted as a function of time by means of equation 4 to self consistency. The half life was calculated at 50% conversion using function 4.

$$Conv. = \left(\frac{I_{Ester}}{1/4(I_{Ac_2O} + I_{Ester} + I_{HNEt_3OAc})}\right) * 100\% \qquad \text{Eq. 2}$$

$$Conv. = \left(1 - \frac{(I_{Anhydride})}{3(I_{Dioxane})}\right) * 200\% \qquad \text{Eq. 3}$$

$$y = A\exp\left(-\frac{(x - x_0)}{t_0}\right) + const. \qquad \text{Eq. 4}$$

Example 1

Pyrido[3,4-b]pyrazine (23): 2.00 g (18.33 mmol) of 3,4-diaminopyridine were added to a solution of 2.82 ml of glyoxal (40 wt. % in water, ρ=1.265 g/ml, 62.48 mmol) in 30 ml of ethanol. The reaction mixture was maintained at an oil bath temperature of 70° C. for 5 hours and after cooling to room temperature the solvent was distilled off on a rotary evaporator. The crude product was purified by flash chromatography (EtOAc/isohexane, 9:1). This gave 2.35 g (17.96 mmol, 98%) of a white powder. $R_f$=0.27 (isohexane/EtOAc, 1:9). $^1$H NMR (200 MHz, $CDCl_3$): δ=7.94 (dd, $^3J$=5.8 Hz, $^4J$=0.6 Hz, 1H, H-7), 8.83 (d, $^3J$=5.8 Hz, 1H, H-8), 8.96 (d, $^3J$=1.6 Hz, 1H, H-3), 9.02 (d, $^3J$=1.6 Hz, 1H, H-2), 9.56 (d, $^4J$=0.6 Hz, 1H, H-5) ppm. $^{13}$C NMR (100 MHz, $CDCl_3$): δ=121.6 (CH, C-7), 138.0 ($C_q$), 145.3 ($C_q$), 147.3 (C—H, C-8), 146.5 (C—H, C-3), 149.2 (CH, C-2), 154.8 (C—H, C-5) ppm. GC-MS (EI): RT 5.45 min, m/e (%): 132 (8), 131 (M$^+$, 100), 104 (25), 77 (13), 50 (10) IR (KBr): ν=3435 (vs), 3092 (w), 3023 (m), 1969 (w), 1758 (w), 1631 (w), 1598 (vs), 1562 (m), 1536 (w), 1488 (s), 1436 (vs), 1416 (m), 1381 (m), 1351 (w), 1290 (w), 1279 (m), 1212 (m), 1201 (m), 1148 (w), 1033 (s), 1014 (s), 972 (w), 959 (vs), 931 (m), 881 (vs), 838 (m), 824 (s), 773 (w), 651 (s), 623 (m), 546 (w), 524 (w), 457 (s) cm$^1$.

Example 2

1,2,3,4-Tetrahydropyrido[3,4-b]pyrazine (26): 2.90 g (0.076 mol) of $NaBH_4$ powder were added to a solution of quinoxaline 23 (2.90 g, 0.022 mol in 100 ml of dry ethanol). The reaction solution was heated to an oil bath temperature of 40° C. and was maintained at this temperature for 24 hours. The reaction solution was subsequently cooled to room temperature and 3 ml of water were added. The inorganic solid was filtered off with suction and washed twice with 20 ml of DCM. The combined organic phases were dried over sodium sulfate and the solvent was distilled off on a rotary evaporator. The crude product obtained was purified by flash chromatography on basic aluminum oxide (EtOAc/MeOH, 10:1). This gave a white foam. $R_f$=0.15 (basic aluminum oxide, 20:1, DCM:MeOH). $^1$H NMR: (200 MHz, CDCl$_3$): δ=3.37 (d, $^3$J=5.8 Hz, 1H, H-3), 3.38 (d, $^3$J=5.8 Hz, 1H, H-2), 6.29 (d, $^3$J=5.4 Hz, 1H, H-8), 7.67 (d, $^3$J=5.4 Hz, 1H, H-7), 7.67 (s, 1H, H-5). $^{13}$C NMR: (100 MHz, CDCl$_3$): δ=40.1 (CH$_2$), 41.0 (CH$_2$), 107.8 (C5), 129.6 (C$_q$), 135.3 (C—H, C7), 140.1 (C$_q$), 141.1 (C—H, C-5). GC-MS RT 8.09 min (EI) m/e (%): 136 (8), 135 (M$^+$ 79), 134 (M$^+$-H$^+$, 100), 133 (10), 132 (7), 131 (2), 120 (4), 107 (7), 105 (4), 94 (2), 93 (7), 80 (2), 79 (3), 78 (4), 67 (4), 66 (2), 53 (2), 52 (2), 52 (3), 51 (2). IR (KBr): ν=3349 (m), 2859 (m), 1593 (s), 1534 (s), 1474 (s), 1344 (s), 1311 (s), 1281 (s), 1256 (w) 1228 (m), 1182 (m), 1102 (m), 1051 (w), 1038 (m), 893 (m), 862 (m), 824 (s), 772 (m) cm$^{-1}$. HRMS (EI) (%) calculated for C$_7$H$_8$N$_3$ (M-H$^+$): 134.0718, found: 134.0709.

Example 3

1-(4-Acetyl-3,4-dihydro-2H-pyrido[3,4-b]pyrazin-1-yl)ethanone (8): 23 ml (24.71 g, 24.20 mol) of acetic anhydride were added to a solution of tetrahydroquinoxaline 26 (1.49 g, 0.011 mol) in 60 ml of pyridine at a temperature of 0° C. The reaction mixture was subsequently heated at 100° C. for 48 hours. After cooling to room temperature, the solvent was distilled off under reduced pressure and the yellow solid was purified by flash chromatography (EtOAc:MeOH, 10:3). This gave 1.93 g (8.80 mmol, 80%) of a pale yellow solid. $^1$H NMR (400 MHz, CDCl$_3$): δ=2.25 (s, 3H, CH$_3$), 2.31 (s, 3H, CH$_3$), 3.90 (ddd, $^2$J=12 Hz, $^3$J=4 Hz, $^3$J=4 Hz, 2H, CH$_2$), 3.94 (ddd, $^2$J=12 Hz, $^3$J=4 Hz, $^3$J=4 Hz, 2H, CH$_2$), 7.67 (s, 1H, H-5), 7.87 (bs, 1H, H-5), 8.32 (d, $^3$J=4 Hz, 1H, H-7), 8.46 (m, 1H, H-8). $^{13}$C NMR (100 MHz, CDCl$_3$): δ=22.3, 22.8 (CH$_3$), 42.1, 46.5 (CH$_2$), 117.4 (C5), 128.2 (C$_q$), 139.0 (C$_q$), 145.7 (C-7), 146.9 (C-8), 168.6 (C=O). GC-MS (EI) RT 9.66 min, m/e (%): 220 (14), 219 (M$^+$, 81), 178 (11), 177 (M$^+$-AcO, 100), 176 (10), 162 (3), 159 (2), 136 (7), 135 (78), 134 (M$^+$-2AcO, 99), 133 (8), 132 (9), 120 (4), 119 (2), 107 (5), 105 (2), 93 (3), 80 (2), 79 (4), 78 (4), 52 (2), 51 (2), 43 (AcO$^+$, 20); IR (neat): ν=2960 (w), 1684 (s) 1654 (vs) 1582 (m) 1494 (s), 1407 (vs), 1330 (m), 1320 (vs), 1277 (m), 1259 (s), 1248 (m), 1217 (s), 1248 (s), 1217 (s), 1179 (m), 1150 (w), 1118 (m), 1064 (m), 1033 (s), 969 (s), 886 (w), 857 (m), 846 (s), 799 (s), 764 (w), 749 (w), 704 (w) cm$^{-1}$. HRMS (EI) calculated for C$_{11}$H$_{13}$N$_3$O$_2$ [M$^+$]: 219.1008; found: 219.0995.

Example 4

1,4-Diethyl-1,2,3,4-tetrahydropyrido[3,4-b]pyrazine (20): 1.56 g (11.69 mmol) of AlCl$_3$ were suspended in 60 ml of MTBE at room temperature. After stirring for 45 minutes, the reaction mixture was cooled to 0° C. and LiAlH$_4$ (1.32 g, 34.65 mmol) was added a little at a time. After the addition was complete and the mixture had been stirred for another 15 minutes, compound 8 (1.00 g, 4.56 mmol) was added and the mixture was stirred at 0° C. for another hour. The reaction mixture was subsequently refluxed for 8 hours and after cooling to room temperature was poured into ice water. The precipitated inorganic solid was filtered off with suction and washed twice with 30 ml of DCM. The aqueous phase was brought to a pH of 12 and extracted three times with 40 ml of DCM. The combined extracts were dried over Na$_2$SO$_4$ and the solvent was distilled off on a rotary evaporator. The crude product was purified by flash chromatography on silica gel (EtOAc/MeOH/NEt$_3$, 10:0.5:1). This gave 0.52 g (60%) of a colorless oil which solidified in the freezer. $R_f$=0.47 (EtOAc/MeOH/NEt$_3$, 10:0.5:1). $^1$H NMR: (400 MHz, CDCl$_3$): δ=1.15 (q, $^3$J=14 Hz, 6H, CH$_3$), 3.22 (m, $^3$J=6 Hz, 2H, H-3), 3.23 (m, $^2$J=14 Hz, 4H, CH$_2$), 3.42 (m, $^3$J=6 Hz, 2H, H-2), 6.34 (d, $^3$J=5.2 Hz, 1H, H-8), 7.69 (s, 1H, H-5), 7.75 (d, $^3$J=5.2 Hz, 1H, H-7). $^{13}$C NMR: (100 MHz, CDCl$_3$): δ=10.1, 10.4 (CH$_3$), 44.6, 46.5 (CH$_2$, C-2, C-3), 44.9, 45.0 (CH$_2$), 104.0 (C-8), 130.5, 130.1 (C$_q$), 131.8 (C-5), 140.7 (C-7). GC-MS (EI): RT 8.63 min, m/e (%): 192 (10), 191 (M$^+$, 100), 190 (4), 177 (8), 176 (95), 175 (5), 162 (11), 161 (8), 160 (5), 148 (13), 147 (10), 146 (8), 135 (2), 134 (9), 133 (6), 131 (8), 121 (2), 119 (4), 118 (3), 107 (3), 104 (2), 92 (2), 91 (2), 80 (8), 77 (4) IR (KBr): ν=3436 (s), 3112 (w), 3019 (w), 2964 (w), 1661 (s), 1686 (vs), 1583 (m), 1497 (m), 1409 (s), 1363 (w), 1332 (m), 1311 (s), 1260 (m), 1249 (w), 1232 (m), 1220 (m), 1180 (m), 1150 (w), 1119 (m), 1064 (m), 1035 (m), 985 (m), 970 (m), 886 (s), 858 (m), 847 (m), 802 (m), 765 (w), 740 (w), 704 (w), 647 (w), 614 (w), 592 (w), 577 (m), 570 (m), 507 (w) cm$^{-1}$. HRMS (EI) calculated for C$_{11}$H$_{17}$N$_3$ [M$^+$]: 191.1422; found: 191.1430.

Example 5

1,4-Dimethy-1,2,3,4-tetrahydropyrido[3,4-b]pyrazine (6): 35 ml of formic acid were added to tetrahydroquinoxaline 26 (1.26 g, 9.32 mmol) while cooling in ice. 12 ml of formaldehyde solution (<37% in water) were subsequently added and the mixture was heated at an oil bath temperature of 110° C. for 48 hours. It was subsequently allowed to cool to room temperature and about 150 ml of 20% strength sodium hydroxide solution were added while cooling in ice. The pH did not exceed 12 during this addition. The mother liquor was extracted overnight with 250 ml of DCM in a liquid/liquid extractor. The organic phase was dried over Na$_2$SO$_4$ and the solvent was distilled off on a rotary evaporator. The crude product was purified by flash chromatograhy on silica gel (EtOAc/MeOH/NEt$_3$, 10:1:1) and basic aluminum oxide (EtOAc/MeOH, 10:1). This gave 0.849 g (5.32 mmol, 57%) of a yellow solid. $R_f$=0.56 (basic alumina, EtOAc/MeOH, 10:1). $^1$H NMR: (400 MHz, CDCl$_3$): δ=2.77 (s, 3H, CH$_3$), 2.82 (s, 3H, CH$_3$), 3.12 (m, 2H, CH$_2$—B), 3.37 (m, 2H, CH$_2$—C), 6.21 (d, $^3$J=5.6 Hz, 1H, H-7), 7.56 (s, 1H, H-5), 7.74 (d, $^3$J=5.6 Hz, 1H, H-8) ppm. $^{13}$C NMR: δ=(75 MHz, CDCl$_3$): 38.0 (N-1-CH$_3$), 39.1 (N-4-CH$_3$), 48.8 (C-3), 49.6 (C-2), 104.0 (C-7), 131.2 (C-5), 132.3 (C-4a), 141.6 (C-7), 142.2 (C-8a) ppm; GC-MS (EI): RT 8.05 min, m/e (%): 164 (8), 163 (M$^+$, 100), 162 (21), 161 (5), 149 (4), 148 (40) 147 (9), 146 (8), 134 (8), 133 (11), 132 (6), 121 (4), 120 (2), 119 (6), 107 (3), 105 (2), 93 (2), 92 (4), 81 (6), 80 (4), 79 (2), 78 (4), 66 (3), 51 (2), 42 (4). IR (neat): ν=3378 (w), 3035 (w), 2979 (w), 2873 (m), 2826 (s), 2792 (w), 1581 (s), 1519 (s), 1466 (s), 1454 (s), 1435 (m), 1416 (m), 1380 (w), 1335 (vs), 1290 (s), 1250 (w), 1235 (vs), 1214 (m), 1172 (s), 1114 (s), 1099 (s), 1069 (s), 1030 (m), 936 (w), 911 (w), 883 (s), 815 (s), 800 (s), 783 (s), 746 (m), 709 (m), 622 (m) cm$^{-1}$. HRMS (EI) calculated for C$_9$H$_{13}$N$_3$ [M$^+$]: 163.1109; found: 163.1089.

Example 6

6,7,8,9-Tetrahydropyrido[3,4-b]quinoxaline (24): 1,2-Cyclohexanedione (1.52 g, 13.93 mmol) was added to a suspension of 1.56 g (13.93 mmol) of 3,4-diaminopyridine in 50 ml of ethanol. The reaction mixture was subsequently heated at an oil bath temperature of 70° C. for 5 hours, then cooled to room temperature and the solvent was then distilled off on a rotary evaporator. The product obtained was purified by flash chromatography using ethyl acetate as eluent. This gave 1.84 g (71%) of a white solid which was stored in a refrigerator and processed further after 1-2 days. Allowing the solid to stand in an open flask in sunlight resulted in the color changing to greyish green. $R_f$=0.25 (EtOAc/hexane, 20:1). $^1$H NMR: (200 MHz, CDCl$_3$): δ=2.05 (m, 4H, H-7,8), 3.18 (m, 4H, H-6,9), 7.79 (d, $^3$J=5.8 Hz, 1H), 8.72 (d, $^3$J=5.8 Hz, 1H), 9.38 (s, 1H) ppm. $^{13}$C NMR (75 MHz, CDCl$_3$): δ=22.8 (CH$_2$, C-7,8), 33.7 (CH$_2$, C-6,9), 121.2 (CH), 136.9 (C$_q$), 144.1 (C$_q$), 146.8 (CH), 153.9 (CH), 156.8 (C$_q$) 159.9 (C$_q$) ppm. GC-MS (EI): RT 8.44 min, m/e (%) 186 (11), 185 (M$^+$, 100), 184 (39), 183 (3), 182 (3), 171 (2), 170 (21), 169 (4), 158 (2), 157 (5), 156 (5) 131 (2), 104 (2), 103 (4), 78 (3), 76 (4), 67 (2), 64 (2), 51 (2), 50 (6); IR (KBr): ν=3435 (vs), 2947 (s), 2864 (m), 1594 (s), 1557 (w), 1461 (w), 1421 (m), 1385 (s), 1365 (w), 1330 (w), 1297 (m), 1211 (m), 1140 (w), 979 (m), 949 (w), 901 (m), 849 (m), 679 (w), 629 (w), 570 (w), 412 (w) cm$^{-1}$. HRMS (EI): calculated for C$_{11}$H$_{11}$N$_3$ 185.0953 [M$^+$], found: 185.0935

Example 7

5,5a,6,7,8,9a,10-Octahydropyrido[3,4-b]quinoxaline (27): 6.13 g (33.09 mmol) of 24 and 100 ml of THF were placed in a 250 ml Schlenk flask. The solution was cooled to −40° C. and 3.09 g (81.42 mmol, 2.5 eq.) of LiAlH$_4$ were added in small portions. The reaction mixture was warmed to room temperature and stirred at room temperature for 32 hours. It was subsequently poured into ice water and the aqueous phase was brought to a pH of 12. The inorganic solid was separated off and washed twice with 40 ml of DCM. The mother liquor was extracted with 250 ml of DCM in a liquid/liquid extractor for 8 hours. The combined organic phases were dried over Na$_2$SO$_4$ and the solvent was distilled off on a rotary evaporator. Flash chromatography (EtOAc/MeOH/NEt$_3$, 10:1:1) of the crude product obtained gave 5.63 g (29.78 mmol, 90%) of a white solid. $R_f$=0.36 (EtOAc/MeOH/NEt$_3$, 10:1:1). $^1$H NMR: (300 MHz, CDCl$_3$): δ=1.32-1.40 (m, 3H), 1.56-1.75 (m, 5H), 3.41 (m, 1H), 3.46 (s, 1H, N—H), 3.51 (m, 1H), 4.20 (s, 1H, N—H), 6.29 (d, 1H, $^3$J=5.4 Hz, H-3), 7.65 (d, 1H, $^3$J=5.4 Hz, H-4), 7.68 (s, 1H, H-1) ppm. $^{13}$C NMR (75 MHz, CDCl$_3$): δ=22.0, 22.2 (C-7,8), 30.4, 30.8 (CH$_2$, C-6,9), 49.2 (CH, C-5a), 50.1 (CH, C-9a), 107.7 (C-4), 128.8 (Cq, C-10a), 134.8 (C-3), 139.2 (Cq, C-4a) 140.7 (C-4) ppm. GC-MS (EI): RT 10.06 min, m/e (%) 190 (13), 189 (M$^+$, 99), 188 (9), 187 (3), 185 (10), 184 (4), 170 (4), 160 (10), 159 (3), 158 (5), 148 (2) 147 (16), 146 (100), 145 (2), 134 (13), 133 (17), 132 (15), 120 (10), 119 (3), 105 (2) 94 (3), 93 (2), 78 (3), 66 (2), 40 (2); IR (neat): ν=3220 (s), 2927 (s), 2852 (s), 2354 (m), 1725 (w), 1595 (vs), 1523 (vs), 1456 (w), 1443 (m), 1403 (w), 1362 (s), 1294 (s), 1269 (s), 1240 (m), 1206 (s), 1175 (s), 1087 (m), 1052 (m), 1003 (m), 938 (m), 884 (m) 810 (vs) 725 (m) cm$^{-1}$. HRMS (EI): calculated for C$_{11}$H$_{15}$N$_3$ 189.1266 [M$^+$], found: 189.1259.

As an alternative, the reaction was also be carried out by the method of Opatz et al. using NaBH$_4$/BH$_3$/H$_2$NCH$_2$CH$_2$OH as reagent, which gave a yield of 74%.[16]

Example 8

1-(10-Acetyl-6,7,8,9,9a,10-hexahydro-5aH-pyrido[3,4-b]quinoxalin-5-yl)ethanone (14): 27 (1.20 g, 6.34 mmol), 40 ml of pyridine, 30 ml (32.36 g, 317 mmol, ρ=1.082 g/ml) of acetic anhydride and 0.234 g (25 mol %) of PPY were introduced into a 250 ml round-bottomed flask while cooling in ice. The reaction mixture was heated to an oil bath temperature of 100° C. and maintained at this temperature for 48 hours. The reaction was followed by TLC on basic aluminum oxide (EtOAC/MeOH, 10:1). After cooling to room temperature, the solvent was distilled off under reduced pressure and the crude product obtained was purified by flash chromatography on basic aluminum oxide (EtOAc/MeOH, 10:1). This gave a dark yellow solid (1.17 g, 4.31 mmol, 68%). $R_f$=0.45 (EtOAC/MeOH, 10:1). $^1$H NMR: (400 MHz, CDCl$_3$): δ=1.34 (m, 4H), 1.60 (d, 4H), 2.23 (s, 3H, H$_3$C—CO—N), 2.27 (s, 3H, H$_3$C—CO—N), 4.74 (m, 1H), 4.85 (m, 1H), 7.25 (d, $^3$J=5.6 Hz, 1H, H-4), 8.41 (d, $^3$J=5.6 Hz, H-3), 8.49 (s, 1H, H-1) ppm. $^{13}$C NMR (75 Hz, CDCl$_3$): δ=21.7, 21.9 (C-7,8), 23.1, 23.6 (H$_3$C—CO—N), 28.4, 28.5 (C-6,9), 55.2, 56.0 (CH, C-5a,9a), 119.6 (C-4), 130.8 (Cq, C-10a), 141.6 (Cq, C-4a), 147.1, 147.2 (C-1, C-3) 169.1, 169.2 (C=O) ppm. GC-MS (EI): RT 10.45 min, m/e (%) 274 (13), 273 (M$^+$, 58), 232 (15), 231 (100), 230 (42), 216 (5), 214 (5), 213 (5), 203 (3), 202 (4), 190 (13), 189 (84), 188 (45), 173 (5), 172 (6), 160 (7), 159 (5), 158 (5), 147 (8), 146 (40) 134 (6), 133 (13), 132 (15), 120 (7), 43 (9); IR (neat): ν=2940 (m), 1660 (vs), 1587 (m), 1559 (w), 1498 (s), 1448 (w), 1427 (w), 1388 (m), 1353 (w), 1337 (m), 1289 (s); 1270 (s), 1248 (s), 1248 (m), 1220 (w), 1183 (w), 1102 (w), 1036 (m), 978 (m), 857 (w), 839 (w) 777 (w) cm$^{-1}$. HRMS (EI): calculated for C$_{11}$H$_{15}$N$_3$ 273.1477 [M$^+$], found: 273.1482.

Example 9

5,10-Diethyl-5,5a,6,7,8,9,9a,10-octahydropyrido[3,4-b]quinoxaline (11): A suspension of 0.77 g (5.80 mmol) of AlCl$_3$ in 30 ml of MTBE was stirred at room temperature for 45 minutes and subsequently cooled to 0° C. and 1.32 g (9.35 mmol) of LiAlH$_4$ were then added in small portions. After the addition was complete and the mixture had been stirred for another 15 minutes, compound 14 (0.64 g, 2.23 mmol) was added and the mixture was stirred at 0° C. for 1 hour. It was subsequently refluxed for 8 hours and then cooled to room temperature and poured into ice water. The inorganic precipitate was filtered off with suction and washed twice with 30 ml of DCM. The aqueous phase was brought to a pH of 12 and extracted three times with 40 ml of DCM. The combined organic phases were dried over Na2SO4 and the solvent was distilled off on a rotary evaporator. The crude product obtained was purified by flash chromatography on silica gel (EtAc/MeOH/NEt$_3$, 10:2:1) and on basic aluminum oxide (EtOAc/MeOH, 10:1). This gave 0.30 g (1.22 mmol, 55%) of a colorless solid. $R_f$=0.32 (basic alumina, EtOAc/MeOH, 10:1). $^1$H NMR: (400 MHz, CDCl$_3$): δ=1.11, 1.13 (t, $^3$J=7.2 Hz, H$_3$C—CH$_2$—N-5, $^3$J=7.2 Hz, H$_3$C—CH$_2$—N-10, 6-H), 1.37 (m, 2H, H-7,8), 1.56 (m, $^3$J$_{aa}$=6.8 Hz, $^3$J$_{ee}$=3.2 Hz, 4H, H-6, H-9, H-7, H-8), 1.76 (m, $^3$J$_{ae}$=3.2 Hz, 1H, H-9), 1.89 (m, $^3$J$_{ae}$=3.2 Hz, 1H), 3.18 (dq, $^3$J=7.2 Hz, $^2$J=14.4 Hz, 2-H, H$_3$C—CH$_{AB}$—N-5, H$_3$C—CH$_{AB}$—N-10), 3.23 (ddd, $^3$J$_{ae}$=2.8 Hz, $^3$J$_{ae}$=3.2 Hz, $^3$J$_{aa}$=6.8 Hz, 1H, H-5a), 3.34 (ddd, $^3$J$_{ae}$=2.8 Hz, $^3$J$_{ae}$=3.2 Hz, $^3$J$_{ae}$=3.2 Hz, H-1, H-9a), 3.43 (dq, $^3$J=7.2 Hz, $^2$J=14.4 Hz, H$_3$C—CH$_{AB}$—N-5, H$_3$C—CH$_{AB}$—N-10, 2H, H-1), 6.33 (d, $^3$J=5.6 Hz, 1H, H-4), 7.67 (s, 1H, H-1), 7.72 (d, 1H, H-3) ppm. $^{13}$C NMR (100 MHz, CDCl$_3$): δ=10.8 (H$_3$C—CH$_2$—N-5), 11.8 (H$_3$C—CH$_2$—N-10), 21.7 (C-7), 22.9 (C-8), 27.3 (C-6), 27.8 (C-9), 40.4 (H$_3$C—CH$_2$—N-5), 41.7 (H$_3$C—CH$_2$—N-10), 52.8 (C-9a), 56.4 (C-5a), 104.3 (C-4), 130.6 (C-10a, C-1), 139.4 (C-3), 141.2 (C-4a) ppm. GC-MS (EI): RT 10.58 min, m/e (%) 246 (18), 245 (M$^+$, 100), 231 (9), 230 (57), 217 (7), 216 (44), 207 (6), 186 (7), 174 (15), 162 (6), 160 (16), 158 (6), 148 (12), 146 (6), 132 (8); IR (neat): ν=3436 (s), 2970 (m), 2860 (vs), 2860 (s), 1628 (w), 1576 (vs), 1513 (vs), 1473 (w), 1447 (m), 1348 (s), 1317 (w), 1267 (s), 1211 (s), 1167 (w), 1125 (w), 1107 (w), 1077 (w), 1059 (w), 1040 (w), 920 (w), 798 (s) 777 (m), 746 (m) cm$^{-1}$. HRMS (EI): calculated for $C_{15}H_{23}N_3$ 245.1892 [M$^+$], found: 245.1889.

Example 10

1-(6,7,8,9,9a,10-Hexahydro-5aH-pyrido[3,4-b]quinoxalin-5-yl)ethanone (28): 27 (1.0 g, 5.28 mmol), 20 ml of DCM, 2.20 ml (15.84 mmol) of $NEt_3$ and 5 mol % of PPY (39 mg, 0.264 mmol) were placed in a 100 ml Schlenk flask. 0.54 ml (5.81 mmol) of acetic anhydride were subsequently added and the reaction mixture was stirred for 30 minutes. The reaction was subsequently stopped by addition of 2 ml of MeOH and stirred for a further 10 minutes. The solvent was distilled off on a rotary evaporator and the crude product obtained was purified by flash chromatography (EtOAc/MeOH/NEt$_3$, 10:1:1). This gave 1 g (4.31 mmol, 82%) of 28. The product obtained contained PPY as impurity and was reacted further without further purification. $R_f$=0.44 (EtOAc/NEt$_3$/MeOH, 10:1:1). $^1$H NMR: (300 MHz, CDCl$_3$): δ=1.44 (m, 5H), 1.76 (m, 3H), 2.29 (s, 3H, H$_3$C—CO—N), 3.59 (m, 1H), 4.07 (m, 1H), 7.08 (bs, 1H, H-4), 7.85 (d, $^3$J=5.4 Hz, 1H, H-3), 7.98 (s, H-1, H-1). $^{13}$C NMR (75 MHz, CDCl$_3$): δ=18.5 (CH$_2$), 23.5 (H$_3$C—CO—N), 24.8, 25.4 (CH$_2$), 31.08 (CH$_2$), 48.9 (C-9a), 118.1 (C$_q$, C-4a), 127.9 (C$_q$, C-10a), 132.2 (C-4), 136.6 (C-1), 138.0 (C-3), 169.0 (C=O) ppm. HRMS (EI): calculated for $C_{13}H_{17}N_3O$ 231.1372 [M$^+$], found: 231.1368.

Example 11

5-Ethyl-5,5a,6,7,8,9a,10-octahydropyrido[3,4-b]quinoxaline (29): 0.619 g (4.64 mmol) of AlCl$_3$ were suspended in 30 ml of THF and the mixture was stirred at room temperature for 45 minutes. It was subsequently cooled to 0° C. and 0.300 g (7.91 mmol) of LiAlH$_4$ were added in small portions. After stirring for another 15 minutes, compound 28 (0.832 g, 3.59 mmol) was added and the mixture was stirred at 0° C. for 1 hour. The reaction mixture was subsequently refluxed for 8 hours and after cooling poured into ice water. The inorganic precipitate was filtered off and washed twice with 30 ml of DCM. The mother liquor was brought to a pH of 12 and extracted three times with 40 ml of DCM. The combined organic phases were dried over Na$_2$SO$_4$ and the solvent was distilled off on a rotary evaporator. The crude product was purified by flash chromatography on silica gel (EtOAc/NEt$_3$, 10:1). This gave 0.430 g (1.98 mmol, 55%) of a white foam. $R_f$=0.24 (EtOAc/NEt$_3$, 10:1). $^1$H NMR: (300 MHz, CDCl$_3$): δ=1.06 (t, $^3$J=7.2 Hz, 3H, H$_3$C—CH2—N-5), 1.25 (m, 2H), 1.54 (m, 5H), 1.78 (m, 1H), 3.20 (m, 4H), 3.79 (s, 1H, N—H), 6.21 (d, $^3$J=5.7 Hz, 1H, H-4), 7.57 (s, H-1, H-1), 7.65 (d, J=5.7 Hz, 1H, H-3). $^{13}$C NMR (75 MHz, CDCl$_3$): δ=12.1 (H$_3$C—CH$_2$—N-5), 19.3 (C-7), 24.8 (C-8), 26.8 (C-6), 30.9 (C-9), 42.8 (H$_3$C—CH$_2$—N-5), 47.8 (C-5a), 58.4 (C-9a), 103.9 (C-4), 129.8 (C$_q$, C-10a), 133.4 (C-1), 138.4 (C$_q$, C-10a), 140.9 (C-3) ppm. GC-MS (EI): RT 10.58 min, m/e (%) 218 (17), 217 (M$^+$, 100), 216 (7), 215 (7), 213 (5), 203 (5), 202 (51), 186 (17), 185 (5), 174 (12), 162 (6), 161 (8), 160 (9), 158 (7), 148 (5); 148 (5), 146 (16), 145 (7), 134 (8), 133 (9), 132 (25), 120 (14), 78 (4); IR (neat): ν=3212 (m), 3093 (w), 2971 (w), 2928 (s), 2851 (s), 1589 (s), 1560 (m), 1505 (vs), 1470 (w), 1442 (m), 1419 (m), 1363 (w), 1280 (vs), 1244 (s), 1210 (m), 1194 (s), 1177 (m), 1108 (m), 1072 (m), 1039 (m), 1007 (w) 968 (w), 897 (w), 886 (w), 795 (s), 740 (m) cm$^{-1}$. HRMS (EI): calculated for $C_{13}H_{19}N_3$ 217.1579 [M$^+$], found: 215.1573.

Example 12

1-(5-Ethyl-5a,6,7,8,9,9a-hexahydro-5H-pyrido[3,4-b]quinoxalin-10-yl)ethanone (30): 29 (0.250 g, 1.15 mmol) and 10 ml of THF were placed in a 100 ml Schlenk flask. The solution was cooled to −78° C., 0.51 ml of n-BuLi (1.27 mmol, 1.1 eq; 2.5 M in hexane) were added and the reaction solution was stirred without cooling for 30 minutes. After 30 minutes, the reaction solution was cooled back down to −78° C. and 0.09 ml (0.109 g, 1.4 mmol, ρ=1.1051 g/ml) of acetyl chloride were added, the cooling bath was removed and the mixture was stirred without cooling for 1 hour. The reaction was subsequently stopped by means of 4 ml and extracted three times with 20 ml of DCM. The combined organic phases were dried over Na$_2$SO$_4$ and the solvent was distilled off on a rotary evaporator. The crude product was purified on silica gel (EtOAc/MeOH, 10:2) to give 48 mg (0.18 mmol, 16%) of a colorless solid. $R_f$=0.16 (EtOAc/NEt$_3$, 10:1). $^1$H NMR: (300 MHz, CDCl$_3$): δ=1.19 (t, $^3$J=7.2 Hz, 3H, H$_3$C—CH$_2$—N-5), 1.24 (m, 2H), 1.45 (m, 2H), 1.58 (m, 2H), 1.74 (m, 1H), 2.18 (m, 1H), 3.34 (m, $^2$J=14.4 Hz, $^3$J=7.2 Hz, 1H, H$_3$C—CH$_{AB}$—N-5), 3.53 (m, 1H, C—H), 3.57 (m, $^2$J=15.2 Hz, $^3$J=7.2 Hz, 1H, H$_3$C—CH$_{AB}$—N-5), 4.90 (bs, 1H, C—H), 6.62 (d, $^3$J=5.6 Hz, 1H, H-4), 8.12 (s, 1H, H-1), 8.08 (d, $^3$J=5.6 Hz, 1H, H-3). $^{13}$C NMR (100 MHz, CDCl$_3$): δ=12.4 (H$_3$C—CH$_2$—N-5), 18.9 (C-7), 22.8 (H$_3$C—CO—N-10), 24.7 (C-8), 25.8 (C-6), 28.5 (C-9), 40.0 (H$_3$C—CH$_2$—N-5), 48.7 (C-9a), 53.7 (C-5a), (C-4), 106.4 (C-4), 120.1 (C$_q$, C-10a), 145.1, 145.2 (C-1, C$_q$, C-4a), 147.1 (C-3), 167.1 (C=O) ppm. GC-MS (EI): RT 10.39 min, m/e (%) 260 (11), 259 (M$^+$, 100), 230 (8), 218 (9), 217 (79), 216 (40), 203 (4), 202 (23), 203 (3), 202 (23), 201 (4), 189 (6), 188 (31), 187 (4), 186 (3), 174 (11), 162 (4), 161 (6), 160 (5), 158 (4), 148 (5), 146 (6), 136 (3), 132 (4), 131 (12), 120 (6), 43 (3); IR (neat): ν= 3398 (s), 2933 (s), 2863 (m), 1731 (m), 1637 (vs), 1595 (vs), 1512 (s), 1546 (w), 1449 (m), 1397 (s), 1365 (s), 1334 (m), 1285 (s), 1239. (m), 1198 (m), 1168 (vs), 1123 (w), 1067 (w), 1068 (w), 1016 (w), 802 (vs), 718 (w), 668 (m). HRMS (EI): calculated for $C_{15}H_{21}N_3O$ 259.1685 [M$^+$], found: 259.1687.

Example 13

2,3-Diphenylpyrido[3,4-b]quinoxaline (25) (modified method from literature): 5.51 g (0.026 mmol) of benzil were added to a suspension of 2.86 g (0.026 mol) of 3,4-diaminopyridine in 50 ml of ethanol and the reaction mixture was heated at an oil bath temperature of 70° C. for 6 hours. After cooling to room temperature, the precipitated yellow solid was filtered off (cooling by means of an ice water bath may be useful). Recrystallization from ethanol gave 6.91 g (0.024 mol, 94%) of a pale yellow solid. $^1$H NMR: (400 MHz, CDCl$_3$): δ=7.32-7.42 (m, 6H, 3,4,5-phenyl-H), 7.54-7.51 (m, 4H, 2,6-phenyl-H), 7.98 (dd, $^3$J=6 Hz, $^4$J=0.8 Hz, 1H, 7-H), 8.82 (d, $^3$J=6 Hz, 1H, 8-H), 9.59 (d, $^4$J=0.8 Hz, 1H, 5-H) ppm. $^{13}$C NMR (100 MHz, CDCl$_3$): δ=121.3 (C-7), 128.4, 129.4-129.9 (phenyl-C), 136.3 (C$_q$, C-4a), 143.5 (C$_q$, C-8a), 147.3 (C-8), 154.5 (C-5), 155.3, 157.9 (C$_q$, phenyl-C) ppm. GC-MS (EI): RT 12.34 min, m/e (%) 285 (3), 284 (M$^+$+H, 22), 283 (M$^+$, 100), 282 (46), 206 (2), 181 (3), 180 (25), 179 (17), 154 (3), 153 (5), 152 (3) 142 (1), 141 (8), 140 (4), 127 (2), 104 (3), 103 (14), 102 (3), 78 (2), 77 (5), 76 (4), 51 (2), 50 (9); IR (neat): ν=3061 (w), 1589 (m), 1577 (w), 1538 (w), 1492 (w), 1443 (m), 1419 (w), 1379 (s), 1346 (w), 1326 (m), 1315 (m), 1288 (w), 1211 (m), 1244 (w), 1227 (m), 1212 (w), 1180 (w), 1075 (m), 1058 (m), 1020 (m), 1001 (w), 976 (s), 921 (w), 892 (m), 892 (m), 830 (m), 819 (w), 811 (m), 763 (s), 735 (m), 708 (vs), 629 (s), 615 (m) cm$^{-1}$.

Example 14

2,3-Diphenyl-1,2,3,4-tetrahydropyrido[3,4-b]pyrazine (31): 25 (6.25 g, 22.05 mmol) and 200 ml of ethanol were placed in a 500 ml flask. 6.25 g (165 mmol) of powdered NaBH$_4$ were added to the solution and the reaction mixture was stirred at 40° C. for 48 hours. It was subsequently cooled to room temperature and the reaction was stopped by means of 10 ml of cold water. After stirring for a further 10 minutes, the reaction mixture was extracted twice with 100 ml of DCM and the combined organic phases were dried over Na$_2$SO$_4$. The crude product was purified by flash chromatography on silica gel (EtOAc/NEt$_3$, 10:1). This gave a pale yellow solid. R$_f$=0.23 (EtOAc/NEt$_3$, 10:1); $^1$H NMR: (300 MHz, CDCl$_3$): δ=3.99 (s, 1H, N—H), 4.59 (s, 2H, 2,3-H), 4.62 (s, 1H, N—H), 6.39 (d, $^3$J=5.4 Hz, 1H, 8-H), 6.80 (dd, $^4$J=1.2 Hz, $^3$J=9.3 Hz, 2H, 2,6-phenyl-H), 6.84 (dd, $^4$J=1.2 Hz, $^3$J=9.3 Hz, 2H, 2,6-phenyl-H), 7.12 (m, 6H, 3,4,5-phenyl-H) ppm. $^{13}$C NMR (75 MHz, CDCl$_3$): δ=58.6, 60.1 (C-2,3), 108.0 (C-8), 127.9-128.4 (phenyl-C), 129.8 (C-4a), 139.8 (C$_q$, phenyl-C), 140.0 (C$_q$, C-8a), 134.9 (C-5), 141.3 (C-7) ppm; MS (EI): m/e (%) 288 (22), 287 (M$^+$, 100), 286 (24), 285 (7), 284 (6), 283 (8), 282 (5), 211 (13), 210 (78), 209 (5), 208 (13), 197 (4), 196 (26), 181 (13), 179 (3), 127 (4), 104 (7), 92 (3), 91 (32), 77 (5); IR (neat): ν=3215 (w), 2830 (w), 1596 (s), 1519 (s), 1493 (w), 1466 (w), 1452 (s), 1360 (m), 1290 (s), 1250 (m), 1231 (m), 1174 (s), 1120 (m), 1072 (m), 1050 (w), 1029 (w), 1005 (w), 989 (w), 950 (w), 905 (w), 844 (w), 810 (m), 770 (m), 723 (m), 675 (vs), 668 (w), 645 (w), 618 (m) cm$^{-1}$. HRMS (EI): calculated for C$_{19}$H$_{17}$N$_3$ 287.1422 [M$^+$], found: 287.1402.

Example 15

4-Methyl-2,3-diphenyl-1,2,3,4-tetrahydropyrido[3,4-b]pyrazine (32): In a 100 ml round-bottomed flask, 0.600 g (2.08 mmol) of 31 were dissolved in 15.5 ml (417.6 mmol, ρ=1.22 g/ml) of formic acid while cooling in ice and 5.1 ml of formaldehyde solution (183.6 mmol, ρ=1.22 g/ml, <37% in water) were added. The ice bath was subsequently removed and the mixture was heated at an oil bath temperature of 120° C. for 48 hours. After cooling to 0° C., 50% strength NaOH was added while cooling in ice until the pH of the mother liquor had risen to 12. The mixture was subsequently extracted three times with 50 ml of DCM and the combined organic phases were dried over Na$_2$SO$_4$. After distilling off the solvent on a rotary evaporator, the crude product was purified by flash chromatography on silica gel (CHCl$_3$/isohexane/NEt$_3$, 10:2:1). This gave 0.564 g (1.87 mmol, 90%) of a yellow solid. R$_f$=0.40 (CHCl$_3$/isohexane/NEt$_3$, 10:2:1). $^1$H NMR: (400 MHz, CDCl$_3$): δ=2.85 (s, 3H, CH$_3$), 4.42 (s, 1H, N—H), 4.44 (d, $^3$J=3.6 Hz, 1H, H-3), 4.95 (d, $^3$J=3.6 Hz, 1H, H-2), 6.50 (d, $^3$J=5.2 Hz, 1H, H-8), 6.64 (dd, $^4$J=2.8 Hz, $^3$J=9.2 Hz, 2H, 2,6-phenyl-H), 6.90 (m, 2H, 2,6-phenyl-H) 7.05 (m, 2H, phenyl-H), 7.16 (m, 4H, phenyl-H), 7.82 (s, 1H, H-5), 7.84 (d, $^3$J=5.2 Hz ppm. $^{13}$C NMR (75 MHz, CDCl$_3$): δ=37.2 (CH$_3$), 57.8 (C-3), 67.9 (C-2), 107.6 (C-8), 127.4-128.5 (phenyl-C), 131.3 (C-5), 131.6 (C$_q$, C-4a) 137.4, 138.8 (C$_q$, phenyl-C), 139.9 (C-7, C-8a) ppm. MS (EI): m/e (%) 302 (22), 301 (M$^+$, 100), 300 (5), 286 (5), 224 (10), 222 (4), 211 (13), 210 (87), 209 (3), 208 (6), 195 (11), 181 (9), 179 (3), 178 (3), 178 (3), 150 (7), 132 (3), 127 (3), 120 (3), 104 (4); 92 (3), 91 (31), 85 (4), 83 (6), 78 (4), 77 (5); IR (neat): ν=3200 (w), 3158 (w), 3029 (w), 2948 (w), 2881 (w), 2824 (w), 1578 (s), 1516 (vs), 1491 (m), 1452 (m), 1421 (m), 1374 (w), 1353 (w), 1326 (w), 1294 (w), 1256 (m), 1235 (m), 1199 (w), 1157 (m), 1131 (m), 1103 (w), 1073 (m), 1054 (m), 1031 (m), 1013 (m), 969 (w), 922 (w), 842 (w), 810 (s), 766 (s), 755 (m), 733 (m), 641 (vs) cm$^{-1}$. HRMS (EI): calculated for C$_{20}$H$_{19}$N$_3$ 301.1574 [M$^+$], found: 301.1559.

Example 16

4-(Methyl-2,3-diphenyl-1,2,3,4-tetrahydropyrido[3,4-b]pyrazin-1-yl)ethanone (33): 2.90 g (9.62 mmol) of 32 and 100 ml of MTBE were placed in a 250 ml Schlenk flask. The solution was cooled to −78° C. and 4.62 ml of n-BuLi (11.50 mmol, 1.1 eq; 2.5 M in hexane) were added over a period of 10 minutes. The reaction mixture was stirred without cooling for 30 minutes. It was subsequently cooled to −78° C. and 1.0 ml (0.96 g, 12.55 mmol) of acetyl chloride was added. The reaction mixture was allowed to come to room temperature and stirred for a further 30 minutes, after which the reaction was stopped by addition of 10 ml of water. The mother liquor was extracted three times with DCM and the combined organic phases were dried over Na$_2$SO$_4$. After distilling off the solvent on a rotary evaporator, the crude product was purified either by flash chromatography (CHCl$_3$/isohexane/NEt$_3$, 10:1:1) or by recrystallization from ethyl acetate. This gave 1.2 g (3.49 mmol, 36%) of a white solid. $^1$H NMR: (600 MHz, CDCl$_3$): δ=2.40 (s, 3H, H$_3$C—CO—N), 2.86 (s, 3H, H$_3$C), 4.99 (m, 1H, H-3), 5.35 (d, $^3$J=4.2 Hz, 1H, H-2), 6.53 (d, $^3$J=7.8 Hz, 2H, 2,6-phenyl-H), 6.80 (bs, 2H, 2,6-phenyl-H), 7.08 (t, 2H, $^3$J=7.2 Hz, phenyl-H) 7.17 (t, $^3$J=6.0 Hz, 2H, phenyl-H), 7.22 (t, $^3$J=6.0 Hz, 1H, phenyl-H), 7.25 (t, $^3$J=6.0 Hz, 1H, phenyl-H), 8.03 (d, $^3$J=6.6 Hz, 1H, H-8), 8.17 (s, 1H, H-5), 8.41 (d, $^3$J=6.6 Hz, 1H, H-7) ppm. $^{13}$C NMR (150 MHz, CDCl$_3$): δ=24.60 (H$_3$C—CO—N), 36.9 (H$_3$C), 61.8 (C-3), 63.8 (C-2), 116.9 (C-8), 124.6 (C-5), 128.4-128.9 (phenyl-C), 134.7 (C$_q$, C-8a), 138.7 (C$_q$, C-4a), 171.0 (C=O) ppm; GC-MS (EI): RT 1.22 min, m/e (%) 345 (3), 344 (27), 343 (M$^+$, 100), 315 (6), 302 (7), 301 (41), 300 (84), 224 (6), 223 (4), 222 (5), 211 (4), 210 (27), 208 (9), 195 (6), 181 (9), 179 (4), 178 (4), 146 (4), 118 (15), 104 (5); 92 (9), 91 (94), 78 (4), 77 (4), 43 (6); IR (neat): ν=2428 (m), 2039 (w), 1688 (s), 1613 (w), 1534 (s), 1492 (m), 1454 (w), 1388 (m), 1364 (m), 1345 (m), 1317 (w), 1292 (w), 1292 (w), 1272 (w), 1227 (vs), 1209 (vs), 1122 (w), 1103 (m), 1078 (m), 1028 (m), 998 (m), 822 (s), 799 (m), 768 (m), 704 (m), 691 (m), 638 (w) cm$^{-1}$. HRMS (EI): calculated for C$_{22}$H$_{23}$N$_3$O 343.1685 [M$^+$], found: 343.1699.

Example 17

1-Ethyl-4-methyl-2,3-diphenyl-1,2,3,4-tetrahydropyrido[3,4-b]pyrazine (34): 0.575 g (4.320 mmol) of AlCl$_3$ was suspended in 20 ml of THF at room temperature and the mixture was subsequently stirred at this temperature for 45 minutes. It was subsequently cooled to 0° C. and 0.277 g (7.290 mmol) of LiAlH$_4$ were added in small portions. After the addition was complete, the reaction mixture was stirred for a further 15 minutes and 33 (1.00 g, 3.32 mmol) was added. The mixture was stirred at 0° C. for 1 hour and subsequently refluxed for 12 hours. The reaction mixture was then cooled to room temperature and poured into ice water. The inorganic precipitate was filtered off and the mother liquor was extracted with DCM. The combined organic phases were dried over Na$_2$SO$_4$ and the crude product obtained was purified by flash chromatography (EtOAc/

MeOH/NEt₃, 10/1/0.5). This gave 0.580 g (1.76 mmol, 53%) of a yellow solid. $R_f$=0.57 (EtOAc/MeOH/NEt3, 10/1/0.5). ¹H NMR: (400 MHz, CDCl₃): δ=1.05 (t, ³J=7.2 Hz, 3H, H₃C—CH₂—N), 2.71 (s, 3H, H₃C), 3.17 (qd, ²J=14.8 Hz, ³J=7.2 Hz, 1H, CH₃—CH$_{AB}$—N), 3.38 (qd, ²J=14.8 Hz, ³J=7.2 Hz, 1H, CH₃—CH$_{AB}$—N), 4.40 (d, ³J=3.6 Hz, 1H, H-3), 4.55 (d, ³J=3.6 Hz, 1H, H-2), 6.52 (d, 1H, ³J=5.6 Hz, H-8) 6.73 (m, 4H, phenyl-H), 7.07 (t, ³J=7.2 Hz, 2H, phenyl-H), 7.11 (t, ³J=8 Hz, 2H, phenyl-H), 7.16 (m, 2H, phenyl-H), 7.92 (s, 1H, H-5), 7.96 (d, ³J=5.6 Hz, 1H, H-7) ppm. ¹³C NMR (100 MHz, CDCl₃): δ=11.1 (H₃C—CH₂—N), 37.1 (H₃C—N), 43.3 (H₃C—CH₂—N), 65.7 (C-2), 66.0 (C-3), 104.3 (C-8), 127.7-129.3 (phenyl-C), 133.0 (C-5), 133.3 (C$_q$, C-8a), 137.8, 138.6 (C$_q$, phenyl-C), 140.8 (C$_q$, C-8a), 141.0 (C-7) ppm. GC-HR-ESI-MS: RT 0.53-1.43 min, calculated for C₄₄H₄₇N₆ 659.3862 [2M⁺+H], found: 659.3823, calculated for C₂₂H₂₄N₃ 330.1970 [M⁺+H] found: 330.1940; IR (neat): ν=2965 (w), 2818 (w), 1578 (s), 1518 (vs), 1492 (m), 1452 (s), 1430 (w), 1371 (m), 1356 (m), 1308 (m), 1286 (m), 1266 (s), 1241 (s), 1215 (vs), 1165 (m), 1119 (m), 1067 (s), 1023 (s), 884 (w), 867 (w), 828 (w), 810 (s), 764 (s), 749 (m), 705 (vs), 660 (w), 615 (w) cm⁻¹.

The invention claimed is:

1. A compound of formula I

I wherein
$R^1$ is a $C_{1-10}$ alkyl group or a $C_{1-10}$ acyl group;
$R^2$ is a $C_{1-10}$ alkyl group; and
$R^3$, $R^4$, $R^5$ and $R^6$ are each, independently of one another, H, a $C_{1-10}$ alkyl group, or phenyl; or any one of $R^3$ or $R^4$, together with any one of $R^5$ or $R^6$, and the carbons to which they are attached, define a $C_{3-10}$ cycloalkyl ring.

2. The compound of claim 1 in which at least one of the radicals $R^3$, $R^4$, $R^5$ and $R^6$ is not H.

3. The compound of claim 1 in which at least one of the radicals $R^3$, $R^4$, $R^5$ and $R^6$ is a phenyl group or the two radicals $R^3$ and $R^5$ each represent H and the two radicals $R^4$ and $R^6$ together represent 1,4-butanediyl so as to form a 6-membered ring.

4. The compound of claim 1 in which the two radicals $R^4$ and $R^5$ are located in a cis position relative to one another so as to give a compound of formula Ia:

Ia wherein
$R^3$ and $R^6$ are each, independently of one another, H, a $C_{1-10}$ alkyl group, or phenyl;
$R^4$ and $R^5$ are each, independently of one another, a $C_{1-10}$ alkyl group or phenyl.

5. The compound of claim 1 in which R' and $R^2$ are each ethyl, $R^3$ and $R^6$ are each H and $R^4$ and $R^5$ together are 1,4-butanediyl so as to form a 6-membered ring.

6. A pharmaceutical composition or herbicide composition comprising the compound of claim 1 and a pharmaceutically or herbicidally acceptable carrier, adjuvant, or excipient.

7. A process for preparing the compound of claim 1 comprising:
a) reacting 3,4-diaminopyridine with a 1,2-dicarbonyl compound to form a diimine;
b) reducing the diimine to a diamine; and
c) replacing the hydrogen atoms on the nitrogens at positions 3 and 4 of the pyridine ring.

8. The process of claim 7 wherein N-alkylation is effected by a two-stage synthesis comprising acylation of the nitrogen atom to form an amide followed by reduction of the amide to form an amine.

* * * * *